(12) United States Patent
Denham et al.

(10) Patent No.: US 8,551,140 B2
(45) Date of Patent: Oct. 8, 2013

(54) METHOD AND APPARATUS FOR COUPLING SOFT TISSUE TO BONE

(75) Inventors: Gregory J. Denham, Warsaw, IN (US); Kevin T. Stone, Winona Lake, IN (US); Frank O. Bonnarens, Prospect, KY (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 5 days.

(21) Appl. No.: 13/181,729

(22) Filed: Jul. 13, 2011

(65) Prior Publication Data
US 2011/0270306 A1 Nov. 3, 2011

Related U.S. Application Data

(60) Division of application No. 12/196,405, filed on Aug. 22, 2008, now Pat. No. 8,128,658, which is a continuation-in-part of application No. 11/541,506, filed on Sep. 29, 2006, now Pat. No. 7,601,165, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned.

(51) Int. Cl.
*A61B 17/04* (2006.01)

(52) U.S. Cl.
USPC .......................................... 606/232; 606/228

(58) Field of Classification Search
USPC ............................... 606/232, 228; 623/13.14
See application file for complete search history.

(56) References Cited

U.S. PATENT DOCUMENTS

| RE26,501 E | 12/1859 | Kendrick et al. |
|---|---|---|
| 65,499 A | 6/1867 | Miller |
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

"Arthroscopic Meniscal Repair using the Meniscal Cinch™", Surgical Technique brochure. (2008) Arthrex® 6 sheets.

(Continued)

*Primary Examiner* — Corrine M McDermott
*Assistant Examiner* — Alexander Orkin
(74) *Attorney, Agent, or Firm* — Harness, Dickey

(57) ABSTRACT

A method and apparatus for coupling a soft tissue implant into a locking cavity formed within a bone is disclosed. A bone engaging fastener is coupled to bone. A second fastener is coupled to a suture construction. The second fastener is coupled to the first fastener. Soft tissue is coupled to the suture construction.

21 Claims, 20 Drawing Sheets

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |

| | | | | | |
|---|---|---|---|---|---|
| 4,196,883 A | 4/1980 | Einhorn et al. | 4,714,475 A | 12/1987 | Grundei et al. |
| 4,210,148 A | 7/1980 | Stivala | 4,716,893 A | 1/1988 | Fischer et al. |
| 4,235,161 A | 11/1980 | Kunreuther | 4,719,671 A | 1/1988 | Ito et al. |
| 4,235,238 A | 11/1980 | Ogiu et al. | 4,719,917 A | 1/1988 | Barrows et al. |
| 4,237,779 A | 12/1980 | Kunreuther | 4,723,540 A | 2/1988 | Gilmer, Jr. |
| 4,243,037 A | 1/1981 | Smith | 4,724,839 A | 2/1988 | Bedi et al. |
| 4,249,525 A | 2/1981 | Krzeminski | 4,728,332 A | 3/1988 | Albrektsson |
| 4,263,913 A | 4/1981 | Malmin | 4,738,255 A | 4/1988 | Goble et al. |
| 4,265,246 A | 5/1981 | Barry | 4,739,751 A | 4/1988 | Sapega et al. |
| 4,273,117 A | 6/1981 | Neuhauser et al. | 4,741,330 A | 5/1988 | Hayhurst |
| 4,275,717 A | 6/1981 | Bolesky | 4,741,336 A | 5/1988 | Failla et al. |
| 4,287,807 A | 9/1981 | Pacharis et al. | 4,744,353 A | 5/1988 | McFarland |
| 4,291,698 A | 9/1981 | Fuchs et al. | 4,744,793 A | 5/1988 | Parr et al. |
| 4,301,551 A | 11/1981 | Dore et al. | 4,750,492 A | 6/1988 | Jacobs |
| 4,307,723 A | 12/1981 | Finney | 4,760,843 A | 8/1988 | Fischer et al. |
| 4,312,337 A | 1/1982 | Donohue | 4,760,844 A | 8/1988 | Kyle |
| 4,316,469 A | 2/1982 | Kapitanov et al. | 4,760,848 A | 8/1988 | Hasson |
| 4,326,531 A | 4/1982 | Shimonaka et al. | 4,770,663 A | 9/1988 | Hanslik et al. |
| 4,345,601 A | 8/1982 | Fukuda | 4,772,261 A | 9/1988 | Von Hoff et al. |
| 4,349,027 A | 9/1982 | DiFrancesco | 4,772,286 A | 9/1988 | Goble et al. |
| 4,388,921 A | 6/1983 | Sutter et al. | 4,773,910 A | 9/1988 | Chen et al. |
| 4,400,833 A | 8/1983 | Kurland | 4,775,380 A | 10/1988 | Seedhom et al. |
| 4,402,445 A | 9/1983 | Green | 4,776,328 A | 10/1988 | Frey et al. |
| 4,409,974 A | 10/1983 | Freedland | 4,781,190 A | 11/1988 | Lee et al. |
| 4,438,769 A | 3/1984 | Pratt et al. | 4,784,126 A | 11/1988 | Hourahane et al. |
| 4,441,489 A | 4/1984 | Evans et al. | 4,787,882 A | 11/1988 | Claren et al. |
| 4,454,875 A | 6/1984 | Pratt et al. | 4,790,297 A | 12/1988 | Luque et al. |
| 4,462,395 A | 7/1984 | Johnson | 4,793,363 A | 12/1988 | Ausherman et al. |
| 4,463,753 A | 8/1984 | Gustilo | 4,809,695 A | 3/1989 | Gwathmey et al. |
| 4,473,102 A | 9/1984 | Ohman et al. | 4,813,406 A | 3/1989 | Ogle, II |
| 4,484,570 A | 11/1984 | Sutter et al. | 4,823,794 A | 4/1989 | Pierce |
| 4,489,446 A | 12/1984 | Reed | 4,828,562 A | 5/1989 | Kenna |
| 4,493,323 A | 1/1985 | Albright et al. | 4,832,026 A | 5/1989 | Jones |
| 4,496,468 A | 1/1985 | House et al. | 4,834,098 A | 5/1989 | Jones |
| 4,505,274 A | 3/1985 | Speelman | 4,838,282 A | 6/1989 | Strasser et al. |
| 4,509,516 A | 4/1985 | Richmond | 4,841,960 A | 6/1989 | Garner |
| 4,531,522 A | 7/1985 | Bedi et al. | 4,851,005 A | 7/1989 | Hunt et al. |
| 4,532,926 A | 8/1985 | O'Holla | 4,858,608 A | 8/1989 | McQuilkin et al. |
| 4,534,350 A | 8/1985 | Golden et al. | 4,860,513 A | 8/1989 | Whitman |
| 4,535,764 A | 8/1985 | Ebert | 4,863,383 A | 9/1989 | Grafelmann et al. |
| 4,537,185 A | 8/1985 | Stednitz | 4,870,957 A | 10/1989 | Goble et al. |
| 4,549,545 A | 10/1985 | Levy | 4,873,976 A | 10/1989 | Schreiber |
| 4,549,652 A | 10/1985 | Free | 4,887,601 A | 12/1989 | Richards |
| 4,561,432 A | 12/1985 | Mazor | 4,890,615 A | 1/1990 | Caspari et al. |
| 4,564,007 A | 1/1986 | Coombs et al. | 4,893,619 A | 1/1990 | Dale et al. |
| 4,570,623 A | 2/1986 | Ellison et al. | 4,893,974 A | 1/1990 | Fischer et al. |
| 4,573,844 A | 3/1986 | Smith | 4,895,148 A | 1/1990 | Bays et al. |
| 4,576,608 A | 3/1986 | Homsy | 4,896,668 A | 1/1990 | Popoff et al. |
| 4,584,722 A | 4/1986 | Levy et al. | 4,898,156 A | 2/1990 | Gatturna et al. |
| 4,590,928 A | 5/1986 | Hunt et al. | 4,899,743 A | 2/1990 | Nicholson et al. |
| 4,595,007 A | 6/1986 | Mericle | 4,901,721 A | 2/1990 | Hakki |
| 4,596,249 A | 6/1986 | Freda et al. | 4,922,897 A | 5/1990 | Sapega et al. |
| 4,602,635 A | 7/1986 | Mulhollan et al. | 4,923,461 A | 5/1990 | Caspari et al. |
| 4,602,636 A | 7/1986 | Noiles | 4,927,421 A | 5/1990 | Goble et al. |
| 4,604,997 A | 8/1986 | De Bastiani et al. | 4,946,377 A | 8/1990 | Kovach |
| 4,605,414 A | 8/1986 | Czajka | 4,946,468 A | 8/1990 | Li |
| 4,616,650 A | 10/1986 | Green et al. | 4,950,270 A | 8/1990 | Bowman et al. |
| 4,621,640 A | 11/1986 | Mulhollan et al. | 4,950,285 A | 8/1990 | Wilk |
| 4,624,254 A | 11/1986 | McGarry et al. | 4,960,381 A | 10/1990 | Niznick |
| 4,632,100 A | 12/1986 | Somers et al. | 4,961,741 A | 10/1990 | Hayhurst |
| 4,635,637 A | 1/1987 | Schreiber | 4,968,315 A | 11/1990 | Gatturna |
| 4,636,121 A | 1/1987 | Miller | 4,968,317 A | 11/1990 | Tormala et al. |
| 4,641,652 A | 2/1987 | Hutterer et al. | 4,969,886 A | 11/1990 | Cziffer et al. |
| 4,649,916 A | 3/1987 | Frimberger | 4,974,488 A | 12/1990 | Spralja |
| 4,649,952 A | 3/1987 | Jobe | 4,976,736 A | 12/1990 | White et al. |
| 4,653,486 A | 3/1987 | Coker | 4,978,350 A | 12/1990 | Wagenknecht et al. |
| 4,653,487 A | 3/1987 | Maale | 4,979,956 A | 12/1990 | Silvestrini |
| 4,653,489 A | 3/1987 | Tronzo | 4,983,176 A | 1/1991 | Cushman et al. |
| 4,655,777 A | 4/1987 | Dunn et al. | 4,988,351 A | 1/1991 | Paulos et al. |
| 4,662,068 A | 5/1987 | Polonsky | 4,994,074 A | 2/1991 | Bezwada et al. |
| 4,667,662 A | 5/1987 | Titone et al. | 4,997,433 A | 3/1991 | Goble et al. |
| 4,667,675 A | 5/1987 | Davis | 5,002,550 A | 3/1991 | Li |
| 4,669,473 A | 6/1987 | Richards et al. | 5,002,562 A | 3/1991 | Oberlander |
| 4,683,895 A | 8/1987 | Pohndorf | 5,002,574 A | 3/1991 | May et al. |
| 4,688,561 A | 8/1987 | Reese | 5,007,921 A | 4/1991 | Brown |
| 4,690,169 A | 9/1987 | Jobe | 5,030,224 A | 7/1991 | Wright et al. |
| 4,696,300 A | 9/1987 | Anderson | 5,030,235 A | 7/1991 | Campbell, Jr. |
| 4,705,040 A | 11/1987 | Mueller et al. | 5,035,701 A | 7/1991 | Kabbara |
| 4,708,132 A | 11/1987 | Silvestrini | 5,037,422 A | 8/1991 | Hayhurst et al. |

| | | | | | |
|---|---|---|---|---|---|
| 5,037,426 A | 8/1991 | Goble et al. | 5,268,001 A | 12/1993 | Nicholson et al. |
| 5,041,129 A | 8/1991 | Hayhurst et al. | 5,269,160 A | 12/1993 | Wood |
| 5,046,513 A | 9/1991 | Gatturna et al. | 5,269,783 A | 12/1993 | Sander |
| 5,047,030 A | 9/1991 | Draenert et al. | 5,269,806 A | 12/1993 | Sardelis et al. |
| 5,053,046 A | 10/1991 | Janese | 5,269,809 A | 12/1993 | Hayhurst et al. |
| 5,053,047 A | 10/1991 | Yoon | 5,279,311 A | 1/1994 | Snyder |
| 5,059,201 A | 10/1991 | Asnis | 5,281,422 A | 1/1994 | Badylak et al. |
| 5,059,206 A | 10/1991 | Winters | 5,282,809 A | 2/1994 | Kammerer et al. |
| 5,061,277 A | 10/1991 | Carpentier et al. | 5,282,832 A | 2/1994 | Toso et al. |
| 5,062,344 A | 11/1991 | Gerker | 5,282,867 A | 2/1994 | Mikhail |
| 5,062,843 A | 11/1991 | Mahony, III | 5,285,040 A | 2/1994 | Brandberg et al. |
| 5,064,431 A | 11/1991 | Gilbertson et al. | 5,290,217 A | 3/1994 | Campos |
| 5,071,420 A | 12/1991 | Paulos et al. | 5,290,243 A | 3/1994 | Chodorow et al. |
| 5,074,874 A | 12/1991 | Yoon et al. | 5,306,301 A | 4/1994 | Graf et al. |
| 5,078,731 A | 1/1992 | Hayhurst | 5,312,410 A | 5/1994 | Miller et al. |
| 5,078,843 A | 1/1992 | Pratt | 5,312,422 A | 5/1994 | Trott |
| 5,084,050 A | 1/1992 | Draenert | 5,312,438 A | 5/1994 | Johnson |
| 5,084,058 A | 1/1992 | Li | 5,314,429 A | 5/1994 | Goble |
| 5,085,661 A | 2/1992 | Moss | 5,318,566 A | 6/1994 | Miller |
| 5,087,263 A | 2/1992 | Li | 5,318,575 A | 6/1994 | Chesterfield et al. |
| 5,087,309 A | 2/1992 | Melton, Jr. | 5,318,577 A | 6/1994 | Li |
| 5,089,012 A | 2/1992 | Prou | 5,318,578 A | 6/1994 | Hasson |
| 5,092,866 A | 3/1992 | Breard et al. | 5,320,115 A | 6/1994 | Kenna |
| 5,098,435 A | 3/1992 | Stednitz et al. | 5,320,626 A | 6/1994 | Schmieding |
| 5,100,415 A | 3/1992 | Hayhurst | 5,320,633 A | 6/1994 | Allen et al. |
| 5,100,417 A | 3/1992 | Cerier et al. | 5,324,308 A | 6/1994 | Pierce |
| 5,108,433 A | 4/1992 | May et al. | 5,330,489 A | 7/1994 | Green et al. |
| 5,116,337 A | 5/1992 | Johnson | 5,333,625 A | 8/1994 | Klein |
| 5,116,373 A | 5/1992 | Jakob et al. | 5,334,204 A | 8/1994 | Clewett et al. |
| 5,116,375 A | 5/1992 | Hofmann | 5,336,229 A | 8/1994 | Noda |
| 5,123,913 A | 6/1992 | Wilk et al. | 5,336,231 A | 8/1994 | Adair |
| 5,123,914 A | 6/1992 | Cope | 5,336,240 A | 8/1994 | Metzler et al. |
| 5,127,785 A | 7/1992 | Faucher et al. | 5,339,870 A | 8/1994 | Green et al. |
| 5,129,901 A | 7/1992 | Decoste | 5,342,369 A | 8/1994 | Harryman, II |
| 5,129,902 A | 7/1992 | Goble et al. | 5,346,462 A | 9/1994 | Barber |
| 5,129,904 A | 7/1992 | Illi et al. | 5,350,380 A | 9/1994 | Goble et al. |
| 5,129,906 A | 7/1992 | Ross et al. | RE34,762 E | 10/1994 | Goble et al. |
| 5,139,498 A | 8/1992 | Astudillo Ley | 5,354,298 A | 10/1994 | Lee et al. |
| 5,139,499 A | 8/1992 | Small et al. | 5,356,412 A | 10/1994 | Golds et al. |
| 5,139,520 A | 8/1992 | Rosenberg | 5,356,413 A | 10/1994 | Martins et al. |
| 5,143,498 A | 9/1992 | Whitman | 5,356,417 A | 10/1994 | Golds |
| 5,147,362 A | 9/1992 | Goble | 5,358,511 A | 10/1994 | Gatturna et al. |
| 5,149,329 A | 9/1992 | Richardson | 5,360,431 A | 11/1994 | Puno et al. |
| 5,152,790 A | 10/1992 | Rosenberg et al. | 5,362,294 A | 11/1994 | Seitzinger |
| 5,154,189 A | 10/1992 | Oberlander | 5,364,400 A | 11/1994 | Rego, Jr. et al. |
| 5,156,616 A | 10/1992 | Meadows et al. | 5,366,461 A | 11/1994 | Blasnik |
| 5,163,960 A | 11/1992 | Bonutti | 5,368,599 A | 11/1994 | Hirsch et al. |
| D331,626 S | 12/1992 | Hayhurst et al. | 5,370,661 A | 12/1994 | Branch |
| 5,169,400 A | 12/1992 | Muhling et al. | 5,370,662 A | 12/1994 | Stone et al. |
| 5,176,682 A | 1/1993 | Chow | 5,372,146 A | 12/1994 | Branch |
| 5,178,629 A | 1/1993 | Kammerer | 5,372,604 A | 12/1994 | Trott |
| 5,183,458 A | 2/1993 | Marx | 5,372,821 A | 12/1994 | Badylak et al. |
| 5,192,282 A | 3/1993 | Draenert et al. | 5,374,268 A | 12/1994 | Sander |
| 5,197,987 A | 3/1993 | Koch et al. | 5,374,269 A | 12/1994 | Rosenberg |
| 5,203,784 A | 4/1993 | Ross et al. | 5,379,492 A | 1/1995 | Glesser |
| 5,203,787 A | 4/1993 | Noblitt et al. | 5,383,878 A | 1/1995 | Roger et al. |
| 5,207,679 A | 5/1993 | Li | 5,383,904 A | 1/1995 | Totakura et al. |
| 5,209,753 A | 5/1993 | Biedermann et al. | 5,385,567 A | 1/1995 | Goble |
| 5,209,805 A | 5/1993 | Spraggins | 5,391,171 A | 2/1995 | Schmieding |
| 5,211,647 A | 5/1993 | Schmieding | 5,391,176 A | 2/1995 | de la Torre |
| 5,211,650 A | 5/1993 | Noda | 5,391,182 A | 2/1995 | Chin |
| 5,214,987 A | 6/1993 | Fenton, Sr. | 5,393,302 A | 2/1995 | Clark et al. |
| 5,219,359 A | 6/1993 | McQuilkin et al. | RE34,871 E | 3/1995 | McGuire et al. |
| 5,222,976 A | 6/1993 | Yoon | 5,397,356 A | 3/1995 | Goble et al. |
| 5,224,946 A | 7/1993 | Hayhurst et al. | 5,403,328 A | 4/1995 | Shallman |
| 5,230,699 A | 7/1993 | Grasinger | 5,403,329 A | 4/1995 | Hinchcliffe |
| 5,232,436 A | 8/1993 | Janevski | 5,403,348 A | 4/1995 | Bonutti |
| 5,234,435 A | 8/1993 | Seagrave, Jr. | 5,405,359 A | 4/1995 | Pierce |
| 5,235,238 A | 8/1993 | Nomura et al. | 5,417,691 A | 5/1995 | Hayhurst |
| 5,236,445 A | 8/1993 | Hayhurst et al. | 5,417,698 A | 5/1995 | Green et al. |
| 5,236,461 A | 8/1993 | Forte | 5,417,712 A | 5/1995 | Whittaker et al. |
| 5,242,447 A | 9/1993 | Borzone | 5,423,819 A | 6/1995 | Small et al. |
| 5,246,441 A | 9/1993 | Ross et al. | 5,423,821 A | 6/1995 | Pasque |
| 5,249,899 A | 10/1993 | Wilson | 5,423,823 A | 6/1995 | Schmieding |
| 5,250,053 A | 10/1993 | Snyder | 5,423,860 A | 6/1995 | Lizardi et al. |
| 5,258,015 A | 11/1993 | Li et al. | 5,425,733 A | 6/1995 | Schmieding |
| 5,258,016 A | 11/1993 | DiPoto et al. | 5,425,766 A | 6/1995 | Bowald et al. |
| 5,258,040 A | 11/1993 | Bruchman et al. | 5,433,751 A | 7/1995 | Christel et al. |
| 5,261,908 A | 11/1993 | Campbell, Jr. | 5,437,680 A | 8/1995 | Yoon |

| Patent No. | Date | Name |
|---|---|---|
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,711,969 A | 1/1998 | Patel et al. |
| 5,713,005 A | 1/1998 | Proebsting |

| | | | | | | |
|---|---|---|---|---|---|---|
| 5,713,897 | A | 2/1998 | Goble et al. | 5,893,592 | A | 4/1999 | Schulze et al. |
| 5,713,904 | A | 2/1998 | Errico et al. | 5,895,395 | A | 4/1999 | Yeung |
| 5,713,905 | A | 2/1998 | Goble et al. | 5,897,564 | A | 4/1999 | Schulze et al. |
| 5,713,921 | A | 2/1998 | Bonutti | 5,897,574 | A | 4/1999 | Bonutti |
| 5,716,359 | A | 2/1998 | Ojima et al. | 5,899,902 | A | 5/1999 | Brown et al. |
| 5,716,397 | A | 2/1998 | Myers | 5,899,938 | A | 5/1999 | Sklar et al. |
| 5,718,717 | A | 2/1998 | Bonutti | 5,908,421 | A | 6/1999 | Beger et al. |
| 5,720,747 | A | 2/1998 | Burke | 5,908,436 | A | 6/1999 | Cuschieri et al. |
| 5,720,765 | A | 2/1998 | Thal | 5,910,148 | A | 6/1999 | Reimels et al. |
| 5,720,766 | A | 2/1998 | Zang et al. | 5,911,721 | A | 6/1999 | Nicholson et al. |
| 5,722,976 | A | 3/1998 | Brown | 5,918,604 | A | 7/1999 | Whelan |
| 5,725,529 | A | 3/1998 | Nicholson et al. | 5,921,986 | A | 7/1999 | Bonutti |
| 5,725,549 | A | 3/1998 | Lam | 5,925,008 | A | 7/1999 | Douglas |
| 5,725,556 | A | 3/1998 | Moser et al. | 5,928,231 | A | 7/1999 | Klein et al. |
| 5,725,581 | A | 3/1998 | Brånemark | 5,928,267 | A | 7/1999 | Bonutti et al. |
| 5,725,582 | A | 3/1998 | Bevan et al. | RE36,289 | E | 8/1999 | Le et al. |
| 5,726,722 | A | 3/1998 | Uehara et al. | 5,931,838 | A | 8/1999 | Vito |
| 5,728,107 | A | 3/1998 | Zlock et al. | 5,931,844 | A | 8/1999 | Thompson et al. |
| 5,728,109 | A | 3/1998 | Schulze et al. | 5,931,869 | A | 8/1999 | Boucher et al. |
| 5,728,136 | A | 3/1998 | Thal | 5,935,119 | A | 8/1999 | Guy et al. |
| 5,733,293 | A | 3/1998 | Scirica et al. | 5,935,133 | A | 8/1999 | Wagner et al. |
| 5,733,306 | A | 3/1998 | Bonutti | 5,935,149 | A | 8/1999 | Ek |
| 5,733,307 | A | 3/1998 | Dinsdale | 5,938,668 | A | 8/1999 | Scirica et al. |
| 5,735,875 | A | 4/1998 | Bonutti et al. | 5,941,439 | A | 8/1999 | Kammerer et al. |
| 5,741,259 | A | 4/1998 | Chan | 5,941,900 | A | 8/1999 | Bonutti |
| 5,741,260 | A | 4/1998 | Songer et al. | 5,944,739 | A | 8/1999 | Zlock et al. |
| 5,741,281 | A | 4/1998 | Martin et al. | 5,946,783 | A | 9/1999 | Plociennik et al. |
| 5,743,912 | A | 4/1998 | Lahille et al. | 5,947,915 | A | 9/1999 | Thibodo, Jr. |
| 5,746,751 | A | 5/1998 | Sherts | 5,947,982 | A | 9/1999 | Duran |
| 5,746,752 | A | 5/1998 | Burkhart | 5,947,999 | A | 9/1999 | Groiso |
| 5,746,754 | A | 5/1998 | Chan | 5,948,002 | A | 9/1999 | Bonutti |
| 5,749,898 | A | 5/1998 | Schulze et al. | 5,951,559 | A | 9/1999 | Burkhart |
| 5,755,729 | A | 5/1998 | de la Torre et al. | 5,951,560 | A | 9/1999 | Simon et al. |
| 5,755,791 | A | 5/1998 | Whitson et al. | 5,954,747 | A | 9/1999 | Clark |
| 5,766,176 | A | 6/1998 | Duncan | 5,957,953 | A | 9/1999 | DiPoto et al. |
| 5,766,218 | A | 6/1998 | Arnott | 5,961,520 | A | 10/1999 | Beck, Jr. et al. |
| 5,766,250 | A | 6/1998 | Chervitz et al. | 5,961,521 | A | 10/1999 | Roger et al. |
| 5,769,894 | A | 6/1998 | Ferragamo | 5,961,524 | A | 10/1999 | Crombie |
| 5,769,899 | A | 6/1998 | Schwartz et al. | 5,964,764 | A | 10/1999 | West, Jr. et al. |
| 5,772,673 | A | 6/1998 | Cuny et al. | 5,964,767 | A | 10/1999 | Tapia et al. |
| 5,776,196 | A | 7/1998 | Matsuzaki et al. | 5,964,769 | A | 10/1999 | Wagner et al. |
| 5,782,845 | A | 7/1998 | Shewchuk | 5,964,783 | A | 10/1999 | Grafton et al. |
| 5,782,862 | A | 7/1998 | Bonutti | 5,968,045 | A | 10/1999 | Frazier |
| 5,782,864 | A | 7/1998 | Lizardi | 5,968,047 | A | 10/1999 | Reed |
| 5,782,866 | A | 7/1998 | Wenstrom, Jr. | 5,968,077 | A | 10/1999 | Wojciechowicz et al. |
| 5,785,714 | A | 7/1998 | Morgan et al. | 5,970,697 | A | 10/1999 | Jacobs et al. |
| 5,792,142 | A | 8/1998 | Galitzer | 5,972,006 | A | 10/1999 | Sciaino, Jr. |
| 5,792,149 | A | 8/1998 | Sherts et al. | 5,976,125 | A | 11/1999 | Graham |
| 5,796,127 | A | 8/1998 | Hayafuji et al. | 5,976,127 | A | 11/1999 | Lax |
| 5,797,915 | A | 8/1998 | Pierson, III et al. | 5,980,473 | A | 11/1999 | Korakianitis et al. |
| 5,797,916 | A | 8/1998 | McDowell | 5,980,524 | A | 11/1999 | Justin et al. |
| 5,797,928 | A | 8/1998 | Kogasaka | 5,980,539 | A | 11/1999 | Kontos |
| 5,800,407 | A | 9/1998 | Eldor et al. | 5,980,558 | A | 11/1999 | Wiley |
| 5,810,824 | A | 9/1998 | Chan | 5,980,559 | A | 11/1999 | Bonutti |
| 5,810,848 | A | 9/1998 | Hayhurst | 5,989,252 | A | 11/1999 | Fumex |
| 5,814,056 | A | 9/1998 | Prosst et al. | 5,989,256 | A | 11/1999 | Kuslich et al. |
| 5,814,069 | A | 9/1998 | Schulze et al. | 5,989,282 | A | 11/1999 | Bonutti |
| 5,814,070 | A | 9/1998 | Borzone et al. | 5,993,452 | A | 11/1999 | Vandewalle |
| 5,814,072 | A | 9/1998 | Bonutti | 5,993,476 | A | 11/1999 | Groiso |
| 5,814,073 | A | 9/1998 | Bonutti | 5,997,542 | A | 12/1999 | Burke |
| 5,823,980 | A | 10/1998 | Kopfer | 5,997,552 | A | 12/1999 | Person et al. |
| 5,824,011 | A | 10/1998 | Stone et al. | 5,997,575 | A | 12/1999 | Whitson et al. |
| 5,824,066 | A | 10/1998 | Gross | 6,001,100 | A | 12/1999 | Sherman et al. |
| 5,830,234 | A | 11/1998 | Wojciechowicz et al. | 6,001,106 | A | 12/1999 | Ryan et al. |
| 5,843,084 | A | 12/1998 | Hart et al. | 6,007,538 | A | 12/1999 | Levin |
| 5,845,645 | A | 12/1998 | Bonutti | 6,007,567 | A | 12/1999 | Bonutti |
| 5,846,254 | A | 12/1998 | Schulze et al. | 6,010,525 | A | 1/2000 | Bonutti et al. |
| 5,848,983 | A | 12/1998 | Basaj et al. | 6,016,727 | A | 1/2000 | Morgan |
| 5,849,012 | A | 12/1998 | Abboudi | 6,019,767 | A | 2/2000 | Howell |
| 5,860,973 | A | 1/1999 | Michelson | 6,022,352 | A | 2/2000 | Vandewalle |
| 5,860,978 | A | 1/1999 | McDevitt et al. | 6,022,373 | A | 2/2000 | Li |
| 5,868,740 | A | 2/1999 | LeVeen et al. | 6,024,758 | A | 2/2000 | Thal |
| 5,868,748 | A | 2/1999 | Burke | 6,027,523 | A | 2/2000 | Schmieding |
| 5,868,789 | A | 2/1999 | Huebner | 6,030,410 | A | 2/2000 | Zurbrugg |
| 5,871,484 | A | 2/1999 | Spievack et al. | 6,033,429 | A | 3/2000 | Magovern |
| 5,871,486 | A | 2/1999 | Huebner et al. | 6,033,430 | A | 3/2000 | Bonutti |
| 5,871,490 | A | 2/1999 | Schulze et al. | 6,039,753 | A | 3/2000 | Meislin |
| 5,885,294 | A | 3/1999 | Pedlick et al. | 6,041,485 | A | 3/2000 | Pedlick et al. |
| 5,891,168 | A | 4/1999 | Thal | 6,042,601 | A | 3/2000 | Smith |

| Patent No. | Kind | Date | Inventor |
|---|---|---|---|
| 6,045,551 | A | 4/2000 | Bonutti |
| 6,045,571 | A | 4/2000 | Hill et al. |
| 6,045,572 | A | 4/2000 | Johnson et al. |
| 6,045,573 | A | 4/2000 | Wenstrom, Jr. et al. |
| 6,045,574 | A | 4/2000 | Thal |
| 6,047,826 | A | 4/2000 | Kalinski et al. |
| 6,048,343 | A | 4/2000 | Mathis et al. |
| 6,051,006 | A | 4/2000 | Shluzas et al. |
| 6,051,007 | A | 4/2000 | Hogendijk et al. |
| 6,053,916 | A | 4/2000 | Moore |
| 6,053,921 | A | 4/2000 | Wagner et al. |
| 6,056,752 | A | 5/2000 | Roger |
| 6,056,772 | A | 5/2000 | Bonutti |
| 6,056,773 | A | 5/2000 | Bonutti |
| 6,059,817 | A | 5/2000 | Bonutti et al. |
| 6,059,818 | A | 5/2000 | Johnson et al. |
| 6,062,344 | A | 5/2000 | Okabe et al. |
| 6,066,173 | A | 5/2000 | McKernan et al. |
| 6,068,648 | A | 5/2000 | Cole et al. |
| 6,071,305 | A | 6/2000 | Brown et al. |
| 6,074,403 | A | 6/2000 | Nord |
| 6,077,277 | A | 6/2000 | Mollenauer et al. |
| 6,077,292 | A | 6/2000 | Bonutti |
| 6,080,185 | A | 6/2000 | Johnson et al. |
| 6,086,591 | A | 7/2000 | Bojarski |
| 6,086,592 | A | 7/2000 | Rosenberg et al. |
| 6,086,608 | A | 7/2000 | Ek et al. |
| 6,093,200 | A | 7/2000 | Liu et al. |
| 6,096,060 | A | 8/2000 | Fitts et al. |
| 6,099,527 | A | 8/2000 | Hochschuler et al. |
| 6,099,530 | A | 8/2000 | Simonian et al. |
| 6,099,568 | A | 8/2000 | Simonian et al. |
| 6,102,934 | A | 8/2000 | Li |
| 6,106,545 | A | 8/2000 | Egan |
| 6,110,128 | A | 8/2000 | Andelin et al. |
| 6,113,604 | A | 9/2000 | Whittaker et al. |
| 6,117,160 | A | 9/2000 | Bonutti |
| 6,117,162 | A | 9/2000 | Schmieding et al. |
| 6,123,710 | A | 9/2000 | Pinczewski et al. |
| 6,132,433 | A | 10/2000 | Whelan |
| 6,132,437 | A | 10/2000 | Omurtag et al. |
| 6,139,565 | A | 10/2000 | Stone et al. |
| RE36,974 | E | 11/2000 | Bonutti |
| 6,143,017 | A | 11/2000 | Thal |
| 6,146,406 | A | 11/2000 | Shluzas et al. |
| 6,146,408 | A | 11/2000 | Bartlett |
| 6,149,653 | A | 11/2000 | Deslauriers |
| 6,149,669 | A | 11/2000 | Li |
| 6,152,928 | A | 11/2000 | Wenstrom, Jr. |
| 6,152,934 | A | 11/2000 | Harper et al. |
| 6,152,936 | A | 11/2000 | Christy et al. |
| 6,152,949 | A | 11/2000 | Bonutti |
| 6,156,039 | A | 12/2000 | Thal |
| 6,156,056 | A | 12/2000 | Kearns et al. |
| 6,159,234 | A | 12/2000 | Bonutti et al. |
| 6,165,203 | A | 12/2000 | Krebs |
| 6,168,598 | B1 | 1/2001 | Martello |
| 6,168,628 | B1 | 1/2001 | Huebner |
| 6,179,840 | B1 | 1/2001 | Bowman |
| 6,183,461 | B1 | 2/2001 | Matsuura et al. |
| 6,187,025 | B1 | 2/2001 | Machek |
| 6,190,401 | B1 | 2/2001 | Green et al. |
| 6,190,411 | B1 | 2/2001 | Lo et al. |
| 6,193,754 | B1 | 2/2001 | Seedhom |
| 6,200,318 | B1 | 3/2001 | Har-Shai et al. |
| 6,200,329 | B1 | 3/2001 | Fung et al. |
| 6,200,330 | B1 | 3/2001 | Benderev et al. |
| 6,203,556 | B1 | 3/2001 | Evans et al. |
| 6,203,565 | B1 | 3/2001 | Bonutti et al. |
| 6,203,572 | B1 | 3/2001 | Johnson et al. |
| 6,206,883 | B1 | 3/2001 | Tunc |
| 6,210,376 | B1 | 4/2001 | Grayson |
| 6,214,007 | B1 | 4/2001 | Anderson |
| 6,214,012 | B1 | 4/2001 | Karpman et al. |
| 6,217,580 | B1 | 4/2001 | Levin |
| 6,221,107 | B1 | 4/2001 | Steiner et al. |
| 6,228,096 | B1 | 5/2001 | Marchand |
| 6,231,592 | B1 | 5/2001 | Bonutti et al. |
| 6,235,057 | B1 | 5/2001 | Roger et al. |
| 6,238,395 | B1 | 5/2001 | Bonutti |
| 6,241,734 | B1 | 6/2001 | Scribner et al. |
| 6,241,747 | B1 | 6/2001 | Ruff |
| 6,241,771 | B1 | 6/2001 | Gresser et al. |
| 6,245,081 | B1 | 6/2001 | Bowman et al. |
| 6,254,604 | B1 | 7/2001 | Howell |
| 6,258,091 | B1 | 7/2001 | Sevrain et al. |
| 6,267,766 | B1 | 7/2001 | Burkhart |
| 6,269,716 | B1 | 8/2001 | Amis |
| 6,270,518 | B1 | 8/2001 | Pedlick et al. |
| 6,273,890 | B1 | 8/2001 | Frazier |
| 6,280,474 | B1 | 8/2001 | Cassidy et al. |
| 6,283,973 | B1 | 9/2001 | Hubbard et al. |
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,306,156 | B1 | 10/2001 | Clark |
| 6,306,159 | B1 | 10/2001 | Schwartz et al. |
| 6,309,405 | B1 | 10/2001 | Bonutti |
| 6,312,448 | B1 | 11/2001 | Bonutti |
| 6,315,788 | B1 | 11/2001 | Roby |
| 6,319,271 | B1 | 11/2001 | Schwartz et al. |
| 6,328,758 | B1 | 12/2001 | Tornier et al. |
| 6,342,060 | B1 | 1/2002 | Adams |
| 6,343,531 | B1 | 2/2002 | Amis |
| 6,355,066 | B1 | 3/2002 | Kim |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,479 | B1 | 6/2002 | Justin et al. |
| 6,409,743 | B1 | 6/2002 | Fenton, Jr. |
| 6,413,260 | B1 | 7/2002 | Berrevoets et al. |
| 6,423,073 | B2 | 7/2002 | Bowman |
| 6,423,088 | B1 | 7/2002 | Fenton, Jr. |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,461,373 | B2 | 10/2002 | Wyman et al. |
| 6,464,690 | B1 | 10/2002 | Castaneda et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,478,753 | B2 | 11/2002 | Reay-Young |
| 6,482,210 | B1 | 11/2002 | Skiba et al. |
| 6,485,504 | B1 | 11/2002 | Johnson et al. |
| 6,491,714 | B1 | 12/2002 | Bennett |
| 6,497,901 | B1 | 12/2002 | Royer |
| 6,500,184 | B1 | 12/2002 | Chan et al. |
| 6,500,195 | B2 | 12/2002 | Bonutti |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex |

| Patent | Date | Inventor |
|---|---|---|
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B2 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |

| | | | |
|---|---|---|---|
| 7,066,942 B2 | 6/2006 | Treace | |
| 7,066,944 B2 | 6/2006 | Laufer et al. | |
| 7,081,126 B2 | 7/2006 | McDevitt et al. | |
| 7,087,064 B1 | 8/2006 | Hyde | |
| 7,097,654 B1 | 8/2006 | Freedland | |
| 7,105,010 B2 | 9/2006 | Hart et al. | |
| 7,112,221 B2 | 9/2006 | Harris et al. | |
| 7,118,578 B2 | 10/2006 | West, Jr. et al. | |
| 7,118,583 B2 | 10/2006 | O'Quinn et al. | |
| 7,125,421 B2 | 10/2006 | Tremulis et al. | |
| 7,131,467 B2 | 11/2006 | Gao et al. | |
| 7,137,996 B2 | 11/2006 | Steiner et al. | |
| 7,141,066 B2 | 11/2006 | Steiner et al. | |
| 7,144,414 B2 | 12/2006 | Harvie et al. | |
| 7,153,127 B2 | 12/2006 | Struble et al. | |
| 7,153,307 B2 | 12/2006 | Scribner et al. | |
| 7,153,312 B1 | 12/2006 | Torrie et al. | |
| 7,153,327 B1 | 12/2006 | Metzger | |
| 7,160,285 B2 | 1/2007 | Sklar et al. | |
| 7,160,333 B2 | 1/2007 | Plouhar et al. | |
| 7,172,626 B1 | 2/2007 | Andrews | |
| 7,201,722 B2 | 4/2007 | Krueger | |
| 7,255,675 B2 | 8/2007 | Gertner et al. | |
| 7,255,700 B2 | 8/2007 | Kaiser et al. | |
| 7,255,715 B2 | 8/2007 | Metzger | |
| 7,261,716 B2 | 8/2007 | Strobel et al. | |
| 7,264,634 B2 | 9/2007 | Schmieding | |
| 7,279,008 B2 | 10/2007 | Brown et al. | |
| 7,285,124 B2 | 10/2007 | Foerster | |
| 7,303,577 B1 | 12/2007 | Dean | |
| 7,306,417 B2 | 12/2007 | Dorstewitz | |
| 7,309,355 B2 | 12/2007 | Donnelly et al. | |
| 7,326,222 B2 | 2/2008 | Dreyfuss et al. | |
| 7,329,272 B2 | 2/2008 | Burkhart et al. | |
| 7,361,179 B2 | 4/2008 | Rousseau et al. | |
| 7,377,845 B2 | 5/2008 | Stewart et al. | |
| 7,390,329 B2 | 6/2008 | Westra et al. | |
| 7,390,332 B2 | 6/2008 | Selvitelli et al. | |
| 7,399,018 B1 | 7/2008 | Khachaturian | |
| 7,442,210 B2 | 10/2008 | Segal et al. | |
| 7,465,308 B2 | 12/2008 | Sikora et al. | |
| 7,468,074 B2 | 12/2008 | Caborn et al. | |
| 7,494,506 B2 | 2/2009 | Brulez et al. | |
| D587,807 S | 3/2009 | Wolf et al. | |
| 7,513,910 B2 | 4/2009 | Buskirk et al. | |
| 7,572,298 B2 | 8/2009 | Roller et al. | |
| 7,578,825 B2 | 8/2009 | Huebner | |
| 7,585,311 B2 | 9/2009 | Green et al. | |
| 7,597,705 B2 | 10/2009 | Forsberg et al. | |
| 7,601,165 B2 | 10/2009 | Stone | |
| 7,604,636 B1 | 10/2009 | Walters et al. | |
| 7,608,092 B1 | 10/2009 | Schaffhausen | |
| 7,608,098 B1 | 10/2009 | Stone et al. | |
| 7,615,076 B2 | 11/2009 | Cauthen, III et al. | |
| 7,621,937 B2 | 11/2009 | Pipenhagen et al. | |
| 7,632,287 B2 | 12/2009 | Baker et al. | |
| 7,651,509 B2 | 1/2010 | Bojarski et al. | |
| 7,658,750 B2 | 2/2010 | Li | |
| 7,658,751 B2 | 2/2010 | Stone et al. | |
| 7,670,279 B2 | 3/2010 | Gertner | |
| 7,678,123 B2 | 3/2010 | Chanduszko | |
| 7,695,493 B2 | 4/2010 | Saadat et al. | |
| 7,731,732 B2 | 6/2010 | Ken | |
| 7,736,379 B2 | 6/2010 | Ewers et al. | |
| 7,749,250 B2 | 7/2010 | Stone et al. | |
| 7,758,594 B2 | 7/2010 | Lamson et al. | |
| 7,758,611 B2 | 7/2010 | Kato | |
| 7,776,041 B1 | 8/2010 | Walters | |
| 7,803,173 B2 | 9/2010 | Burkhart et al. | |
| 7,819,895 B2 | 10/2010 | Ginn et al. | |
| 7,828,850 B2 | 11/2010 | Cauthen, III | |
| 7,857,830 B2 | 12/2010 | Stone et al. | |
| 7,875,058 B2 | 1/2011 | Holmes, Jr. | |
| 7,887,586 B2 | 2/2011 | Linares | |
| 7,905,903 B2 | 3/2011 | Stone et al. | |
| 7,905,904 B2 | 3/2011 | Stone et al. | |
| 7,909,851 B2 | 3/2011 | Stone et al. | |
| 7,938,847 B2 | 5/2011 | Fanton et al. | |
| 7,959,650 B2 | 6/2011 | Kaiser et al. | |
| 7,981,140 B2 | 7/2011 | Burkhart | |
| 7,998,203 B2 | 8/2011 | Blum | |
| 8,062,334 B2 | 11/2011 | Green et al. | |
| 8,075,574 B2 | 12/2011 | May et al. | |
| 8,088,130 B2 | 1/2012 | Kaiser et al. | |
| 8,114,127 B2 | 2/2012 | West, Jr. | |
| 8,114,128 B2 | 2/2012 | Cauldwell et al. | |
| 8,118,835 B2 | 2/2012 | Weisel et al. | |
| 8,118,836 B2 | 2/2012 | Denham et al. | |
| 8,128,658 B2 | 3/2012 | Kaiser et al. | |
| 8,137,382 B2 | 3/2012 | Denham et al. | |
| 8,162,997 B2 | 4/2012 | Struhl | |
| 8,167,906 B2 | 5/2012 | Cauldwell et al. | |
| 8,221,454 B2 | 7/2012 | Schaffhausen | |
| 8,231,654 B2 | 7/2012 | Kaiser et al. | |
| 8,251,998 B2 | 8/2012 | Hoeppner et al. | |
| 8,252,022 B2 | 8/2012 | Holman et al. | |
| 8,298,262 B2 | 10/2012 | Stone et al. | |
| 8,303,604 B2 | 11/2012 | Stone et al. | |
| 8,317,825 B2 | 11/2012 | Stone | |
| 2001/0010005 A1 | 7/2001 | Kammerer et al. | |
| 2001/0014825 A1 | 8/2001 | Burke et al. | |
| 2001/0019649 A1 | 9/2001 | Field et al. | |
| 2001/0029387 A1 | 10/2001 | Wolf et al. | |
| 2001/0037131 A1 | 11/2001 | Schmieding et al. | |
| 2001/0037153 A1 | 11/2001 | Rockwood et al. | |
| 2001/0041916 A1 | 11/2001 | Bonutti | |
| 2001/0041937 A1 | 11/2001 | Rieser et al. | |
| 2001/0041938 A1 | 11/2001 | Hein | |
| 2001/0044639 A1 | 11/2001 | Levinson | |
| 2001/0047206 A1 | 11/2001 | Sklar et al. | |
| 2001/0051816 A1 | 12/2001 | Enzerink et al. | |
| 2001/0053934 A1 | 12/2001 | Schmieding | |
| 2002/0001964 A1 | 1/2002 | Choi | |
| 2002/0004669 A1 | 1/2002 | Bartlett | |
| 2002/0007182 A1 | 1/2002 | Kim | |
| 2002/0010513 A1 | 1/2002 | Schmieding | |
| 2002/0013607 A1 | 1/2002 | Lemer | |
| 2002/0013608 A1 | 1/2002 | ElAttrache et al. | |
| 2002/0019649 A1 | 2/2002 | Sikora et al. | |
| 2002/0029066 A1 | 3/2002 | Foerster | |
| 2002/0032465 A1 | 3/2002 | Lemer | |
| 2002/0055780 A1 | 5/2002 | Sklar | |
| 2002/0058966 A1 | 5/2002 | Tormala et al. | |
| 2002/0077659 A1 | 6/2002 | Johnson et al. | |
| 2002/0099411 A1 | 7/2002 | Bartlett | |
| 2002/0111653 A1 | 8/2002 | Foerster | |
| 2002/0120270 A1 | 8/2002 | Trieu et al. | |
| 2002/0120292 A1 | 8/2002 | Morgan | |
| 2002/0123752 A1 | 9/2002 | Schultheiss et al. | |
| 2002/0128654 A1 | 9/2002 | Steger et al. | |
| 2002/0128684 A1 | 9/2002 | Foerster | |
| 2002/0129820 A1 | 9/2002 | Ryan et al. | |
| 2002/0143336 A1 | 10/2002 | Hearn | |
| 2002/0147463 A1 | 10/2002 | Martinek | |
| 2002/0161401 A1 | 10/2002 | Steiner | |
| 2002/0161439 A1 | 10/2002 | Strobel et al. | |
| 2002/0165548 A1 | 11/2002 | Jutley | |
| 2002/0169452 A1 | 11/2002 | Tormala et al. | |
| 2002/0169477 A1 | 11/2002 | Demopulos et al. | |
| 2002/0169478 A1 | 11/2002 | Schwartz et al. | |
| 2002/0173788 A1 | 11/2002 | Bojarski et al. | |
| 2002/0188298 A1 | 12/2002 | Chan | |
| 2002/0193830 A1 | 12/2002 | Bonutti | |
| 2003/0004545 A1 | 1/2003 | Burkhart et al. | |
| 2003/0023268 A1 | 1/2003 | Lizardi | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0065391 A1 | 4/2003 | Re et al. | |
| 2003/0078585 A1 | 4/2003 | Johnson et al. | |
| 2003/0078603 A1 | 4/2003 | Schaller et al. | |
| 2003/0078617 A1 | 4/2003 | Schwartz et al. | |
| 2003/0083662 A1 | 5/2003 | Middleton | |
| 2003/0083694 A1 | 5/2003 | Miller | |
| 2003/0088251 A1 | 5/2003 | Braun et al. | |
| 2003/0088272 A1 | 5/2003 | Smith | |

| | | |
|---|---|---|
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1* | 5/2006 | Weisel et al. ............... 606/232 |

| Pub. No. | Date | Inventor |
|---|---|---|
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |

| | | | | | | |
|---|---|---|---|---|---|---|
| 2011/0046733 | A1 | 2/2011 | Eggli | EP | 0582514 | 2/1994 |
| 2011/0087284 | A1 | 4/2011 | Stone et al. | EP | 0591991 | 4/1994 |
| 2011/0098727 | A1 | 4/2011 | Kaiser et al. | EP | 0598219 | 5/1994 |
| 2011/0106153 | A1 | 5/2011 | Stone et al. | EP | 0611551 A1 | 8/1994 |
| 2011/0160767 | A1 | 6/2011 | Stone et al. | EP | 0627203 | 12/1994 |
| 2011/0160768 | A1 | 6/2011 | Stone et al. | EP | 0651979 | 5/1995 |
| 2011/0208239 | A1 | 8/2011 | Stone et al. | EP | 0669110 | 8/1995 |
| 2011/0208240 | A1 | 8/2011 | Stone et al. | EP | 0686373 | 12/1995 |
| 2011/0213416 | A1 | 9/2011 | Kaiser | EP | 0702933 | 3/1996 |
| 2011/0218625 | A1 | 9/2011 | Berelsman et al. | EP | 0775473 | 5/1997 |
| 2011/0224799 | A1 | 9/2011 | Stone | EP | 0913123 | 5/1999 |
| 2011/0264141 | A1 | 10/2011 | Denham et al. | EP | 0913131 | 5/1999 |
| 2011/0270278 | A1 | 11/2011 | Overes et al. | EP | 99121106 | 10/1999 |
| 2012/0041485 | A1 | 2/2012 | Kaiser et al. | EP | 991210527 | 10/1999 |
| 2012/0041486 | A1 | 2/2012 | Stone et al. | EP | 0995409 | 4/2000 |
| 2012/0046693 | A1 | 2/2012 | Denham et al. | EP | 1013229 | 6/2000 |
| 2012/0053630 | A1 | 3/2012 | Denham et al. | EP | 1093773 | 4/2001 |
| 2012/0059417 | A1 | 3/2012 | Norton et al. | EP | 1093774 | 4/2001 |
| 2012/0059418 | A1 | 3/2012 | Denham et al. | EP | 1555945 | 7/2005 |
| 2012/0089193 | A1 | 4/2012 | Stone et al. | FR | 2622790 | 5/1989 |
| 2012/0095470 | A1 | 4/2012 | Kaiser et al. | FR | 2655840 | 6/1991 |
| 2012/0123474 | A1 | 5/2012 | Zajac et al. | FR | 2682867 | 4/1993 |
| 2012/0123541 | A1 | 5/2012 | Albertorio et al. | FR | 2687911 | 9/1993 |
| 2012/0150297 | A1 | 6/2012 | Denham et al. | FR | 2688689 | 9/1993 |
| 2012/0165866 | A1 | 6/2012 | Kaiser et al. | FR | 2704140 | 10/1994 |
| 2012/0165867 | A1 | 6/2012 | Denham et al. | FR | 2717070 | 9/1995 |
| 2012/0165938 | A1 | 6/2012 | Denham et al. | FR | 2723528 | 2/1996 |
| 2012/0197271 | A1 | 8/2012 | Astorino et al. | FR | 2744010 | 8/1997 |
| 2012/0245585 | A1 | 9/2012 | Kaiser et al. | FR | 2745999 | 9/1997 |
| 2012/0296427 | A1 | 11/2012 | Conner et al. | FR | 2770764 | 5/1999 |
| | | | | GB | 401677 | 11/1933 |
| FOREIGN PATENT DOCUMENTS | | | | GB | 1413477 | 11/1975 |
| AU | | 5850469 | 1/1971 | GB | 1485681 | 9/1977 |
| AU | | 5963869 | 2/1971 | GB | 2083751 | 3/1982 |
| AU | | 1505470 | 11/1971 | GB | 2118474 | 11/1983 |
| AU | | 2223767 | 5/1973 | GB | 2227175 | 7/1990 |
| AU | | 3615171 | 5/1973 | GB | 2253147 A | 9/1992 |
| AU | | 5028569 | 9/1973 | GB | 2312376 | 10/1997 |
| AU | | 7110887 | 10/1987 | GB | 2403416 A | 1/2005 |
| AU | | 639410 | 11/1989 | JP | 5362911 | 5/1978 |
| AU | | 651929 | 8/1994 | JP | 5362912 | 5/1978 |
| DE | | 2529669 | 3/1976 | JP | 5374942 | 6/1978 |
| DE | | 2747312 | 4/1979 | JP | 5378230 | 6/1978 |
| DE | | 2818254 | 10/1979 | JP | 62159647 | 7/1987 |
| DE | | 2919009 | 11/1979 | JP | 62295657 | 12/1987 |
| DE | | 3027138 | 12/1981 | JP | 5269160 | 10/1993 |
| DE | | 3225620 | 2/1983 | JP | 5300917 | 11/1993 |
| DE | | 3136083 | 3/1983 | JP | 751292 | 2/1995 |
| DE | | 233303 | 2/1986 | JP | 10211213 | 8/1998 |
| DE | | 4127550 | 2/1993 | WO | WO-8300615 | 3/1983 |
| DE | | 4302397 | 7/1993 | WO | WO-8603666 | 7/1986 |
| DE | | 29621340 | 5/1998 | WO | WO-8701270 | 3/1987 |
| DE | | 19841252 | 3/2000 | WO | WO-8901767 | 3/1989 |
| EP | | 0108912 | 5/1984 | WO | WO-8909030 | 10/1989 |
| EP | | 0129442 | 12/1984 | WO | WO-8910096 | 11/1989 |
| EP | | 0172130 | 2/1986 | WO | WO-9008510 | 8/1990 |
| EP | | 0241240 | 10/1987 | WO | WO-9203980 | 3/1992 |
| EP | | 0241792 | 10/1987 | WO | WO-9314705 | 8/1993 |
| EP | | 0260970 | 3/1988 | WO | WO-9315694 | 8/1993 |
| EP | | 0270704 | 6/1988 | WO | WO-9502373 | 1/1995 |
| EP | | 0282789 | 9/1988 | WO | WO-9503003 | 2/1995 |
| EP | | 0315371 | 5/1989 | WO | WO-9529637 | 11/1995 |
| EP | | 0317406 | 5/1989 | WO | WO-9532670 | 12/1995 |
| EP | | 0340159 | 11/1989 | WO | WO-9609797 A1 | 4/1996 |
| EP | | 0346183 | 12/1989 | WO | WO-9629029 | 9/1996 |
| EP | | 0349173 | 1/1990 | WO | WO-9737603 | 10/1997 |
| EP | | 0374088 | 6/1990 | WO | WO-9812991 | 4/1998 |
| EP | | 0409364 | 1/1991 | WO | WO-9812992 | 4/1998 |
| EP | | 0415915 | 3/1991 | WO | WO-9822047 | 5/1998 |
| EP | | 0440991 | 8/1991 | WO | WO-9822048 | 5/1998 |
| EP | | 0441065 | 8/1991 | WO | WO-9901084 | 1/1999 |
| EP | | 0451932 | 10/1991 | WO | WO-9912480 | 3/1999 |
| EP | | 0464480 | 1/1992 | WO | WO-9937219 A1 | 7/1999 |
| EP | | 0497079 | 8/1992 | WO | WO-9944544 | 9/1999 |
| EP | | 0502509 | 9/1992 | WO | WO-9952472 A1 | 10/1999 |
| EP | | 0502698 | 9/1992 | WO | WO-0040159 | 7/2000 |
| EP | | 520177 | 12/1992 | WO | WO-0139671 | 6/2001 |
| EP | | 0546726 | 6/1993 | WO | WO-0236020 | 5/2002 |
| EP | | 0574707 | 12/1993 | WO | WO-03005914 A1 | 1/2003 |

| WO | WO-03071962 | | 9/2003 |
| WO | WO-03077772 | | 9/2003 |
| WO | WO-03092551 | A1 | 11/2003 |
| WO | WO-2004091412 | A1 | 10/2004 |
| WO | WO-2005104992 | A1 | 11/2005 |
| WO | WO-2006023661 | A2 | 3/2006 |
| WO | WO-2006055823 | A2 | 5/2006 |
| WO | WO-2007045460 | A2 | 4/2007 |
| WO | WO-2007109280 | A2 | 9/2007 |
| WO | WO-2008002550 | A2 | 1/2008 |
| WO | WO-2008015171 | A1 | 2/2008 |
| WO | WO-2008073588 | A2 | 6/2008 |
| WO | WO-2009012021 | A1 | 1/2009 |
| WO | WO-2011112371 | A1 | 9/2011 |
| WO | WO-2011150238 | A1 | 12/2011 |
| WO | WO-2012134999 | A1 | 10/2012 |
| WO | WO-2012158583 | A1 | 11/2012 |

OTHER PUBLICATIONS

Interview Summary mailed Jul. 14, 2011 for U.S. Appl. No. 12/196,407.
Interview Summary mailed Jul. 14, 2011 for U.S. Appl. No. 12/196,410.
Notice of Allowance mailed Oct. 13, 2011 for U.S. Appl. No. 12/196,410.
Notice of Allowance mailed Oct. 26, 2011 for U.S. Appl. No. 12/196,405.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Office Action mailed Dec. 7, 2011 for U.S. Appl. No. 12/589,168.
Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
US 6,238,418, 5/2001, Schwartz, et al. (withdrawn).
"AperFix® System Surgical Technique Guide. Single Tunnel Double Bundle.™" Cayenne Medical brochure. (Aug. 2008) 8 sheets.
"Bio-lntrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.
"Suture Tensioner w/Tensiometer," Arthrex®, Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Office Action mailed Oct. 24, 2012 for U.S. Appl. No. 13/399,125.
Office Action mailed Sep. 21, 2012 for U.S. Appl. No. 13/098,897.
Office Action mailed Sep. 24, 2012 for U.S. Appl. No. 13/098,927.
Office Action mailedOct. 2, 2012 for U.S. Appl. No. 13/181,729.

Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.

* cited by examiner

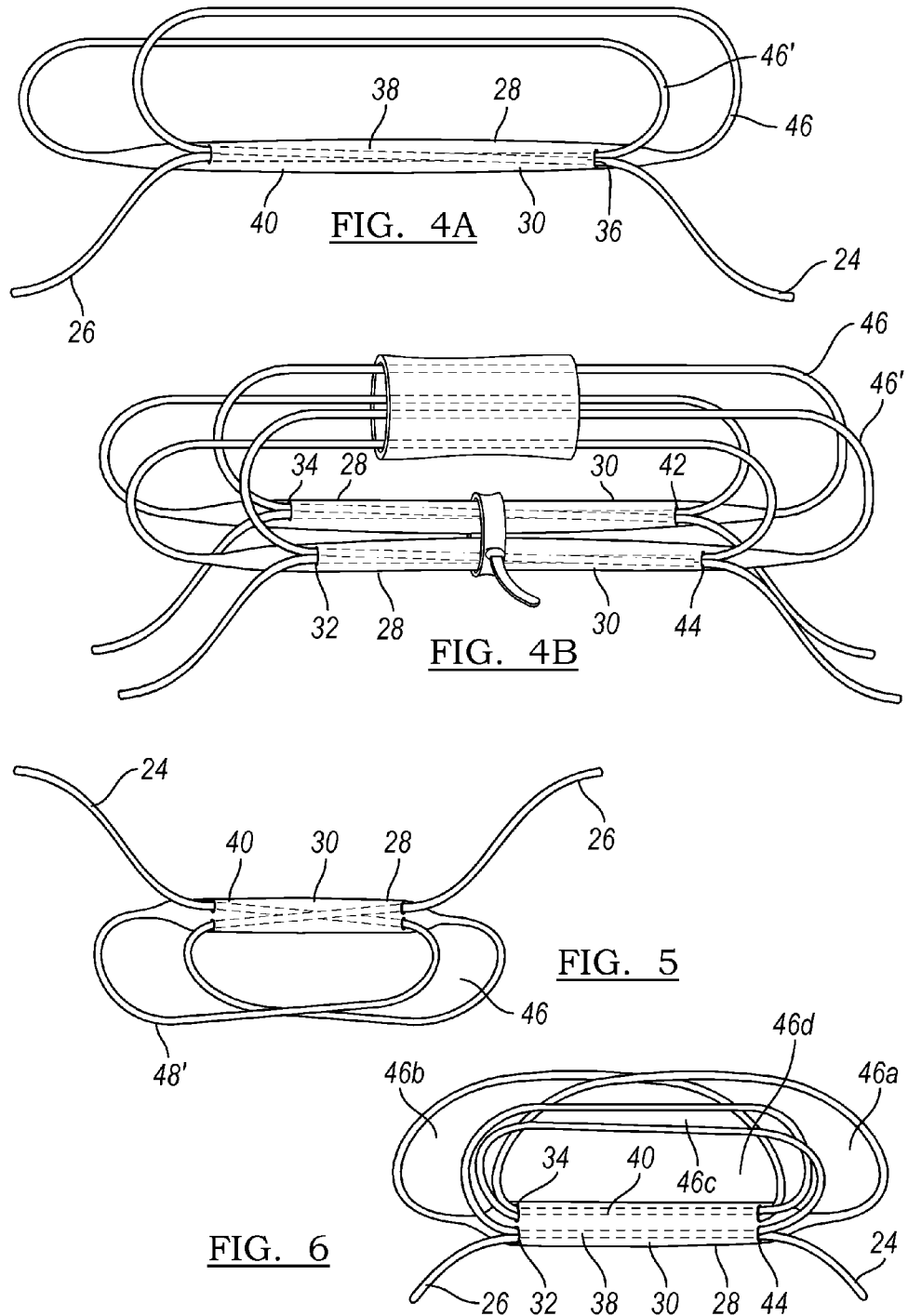

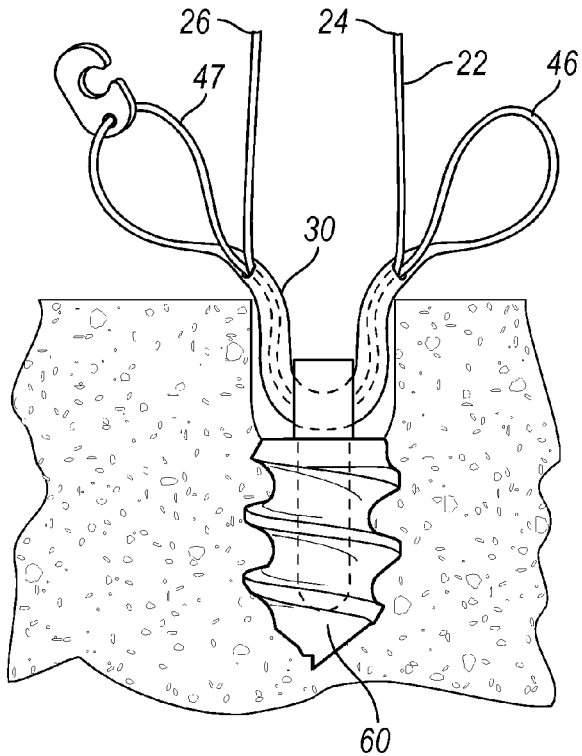
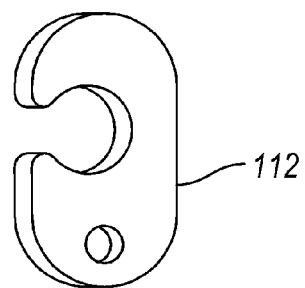
FIG. 16B
FIG. 16A
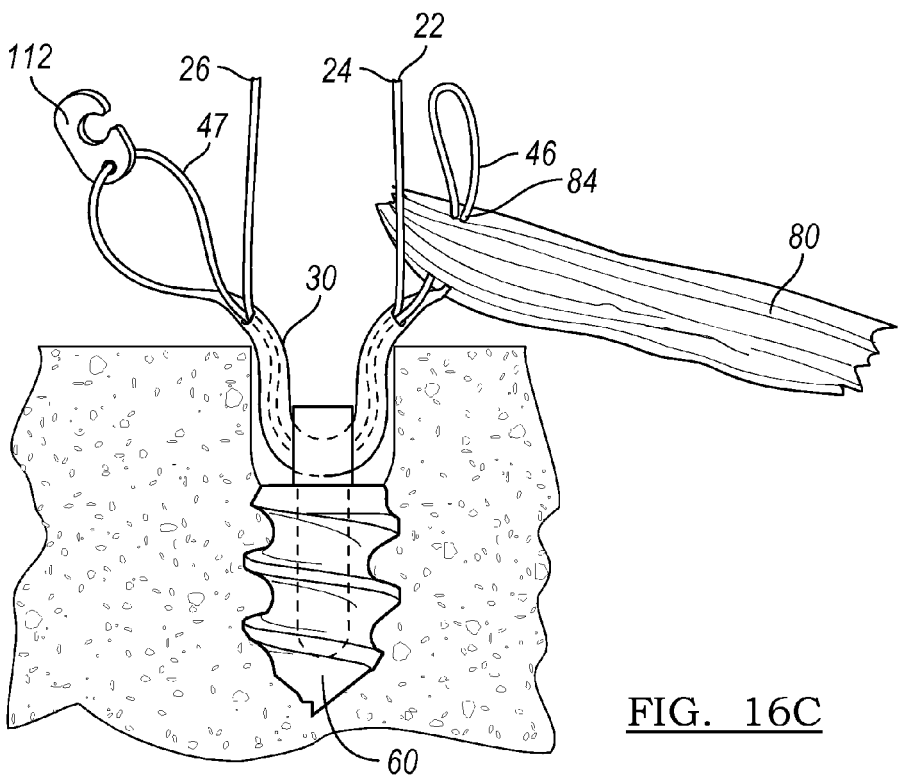
FIG. 16C

METHOD AND APPARATUS FOR COUPLING SOFT TISSUE TO BONE

CROSS-REFERENCE TO RELATED APPLICATIONS

This application is a divisional of U.S. patent application Ser. No. 12/196,405 filed on Aug. 22, 2008, now U.S. Pat. No. 8,128,658, which is a continuation-in-part application of: (a.) U.S. patent application Ser. No. 11/541,506 filed on Sep. 29, 2006, now U.S. Pat. No. 7,601,165 issued on Oct. 13, 2009; (b.) U.S. patent application Ser. No. 12/014,399 filed on Jan. 15, 2008, now U.S. Pat. No. 7,909,851 issued on Mar. 22, 2011; (c.) U.S. patent application Ser. No. 12/014,340 filed on Jan. 15, 2008, now U.S. Pat. No. 7,905,904 issued on Mar. 15, 2011; (d.) U.S. patent application Ser. No. 11/935,681 filed on Nov. 6, 2007, now U.S. Pat. No. 7,905,903 issued on Mar. 15, 2011; (e.) U.S. patent application Ser. No. 11/869,440 filed on Oct. 9, 2007, now U.S. Pat. No. 7,857,830 issued on Dec. 28, 2010; (f.) U.S. patent application Ser. No. 11/784,821 filed on Apr. 10, 2007; (g.) U.S. patent application Ser. No. 11/347,661 filed on Feb. 3, 2006, now U.S. Pat. No. 7,749,250 issued on Jul. 6, 2010; and (h.) U.S. patent application Ser. No. 11/347,662 filed on Feb. 3, 2006, now abandoned. The disclosures of the above applications are incorporated herein by reference.

FIELD

The present disclosure relates to method of coupling soft tissue to bone and, more particularly, to a method and apparatus using a plurality of fasteners and suture cinch loop construction to couple soft tissue to a bone.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

To overcome the aforementioned deficiencies, a method for configuring a braided tubular suture and a suture configuration are disclosed. The method includes passing a first end of the suture through a first aperture into a passage defined by the suture and out a second aperture defined by the suture so as to place the first end outside of the passage. A second end of the suture is passed through the second aperture into the passage and out the first aperture so as to place the second end outside of the passage.

A method of surgically implanting a suture construction in a bone is disclosed. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A fastener is coupled to bone. Soft tissue is then passed through the first and second loops. The locking member is coupled to the fastener. Tension is applied onto the first and second ends to constrict the first and second loops about the soft tissue.

In another embodiment, a method of surgically implanting a suture is disclosed. The suture is passed through a bore defined by a first fastener. A suture construction is formed by passing the suture through a bore defined by a locking member. A first end of the suture is passed through a first aperture within the suture into a passage defined by the suture and out a second aperture defined by the suture so as to place the first end outside of the passage and define a first loop. A second end of the suture is then passed through the second aperture into the passage and out the first aperture so as to place the second end outside of the passage, and define a second loop. A second fastener is coupled between the first and second loops. After the fastener is coupled to the patient, tension is applied onto the first and second ends to constrict at least one of the first and second loops about the soft tissue.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 4A and 4B represent alternate suture configurations;

FIGS. 5-7 represent further alternate suture configurations;

FIGS. 16A-16D represent yet another method for coupling soft tissue to bone;

DETAILED DESCRIPTION

Figure 1:
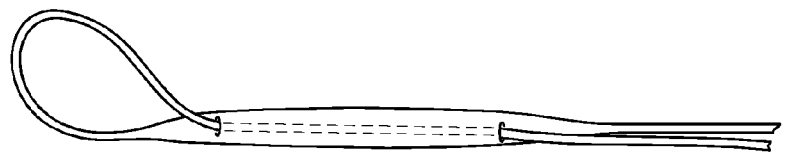
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
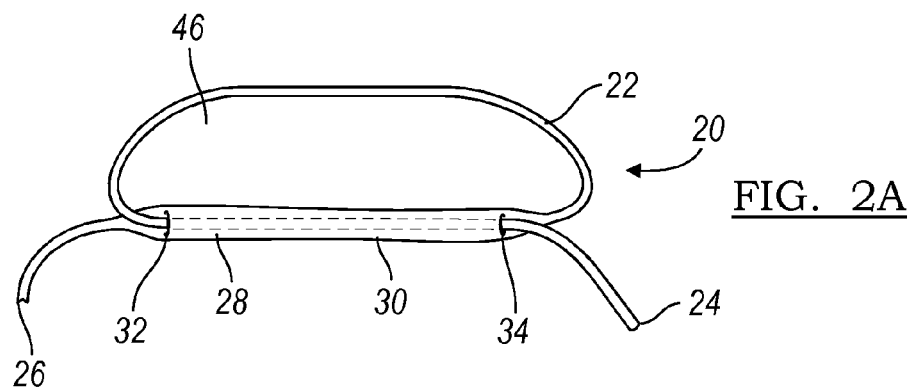
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
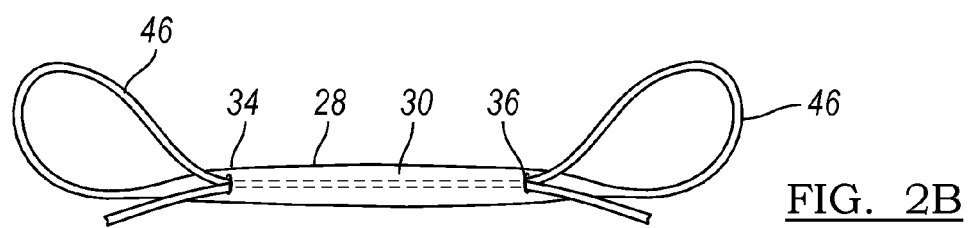
Figure 3:
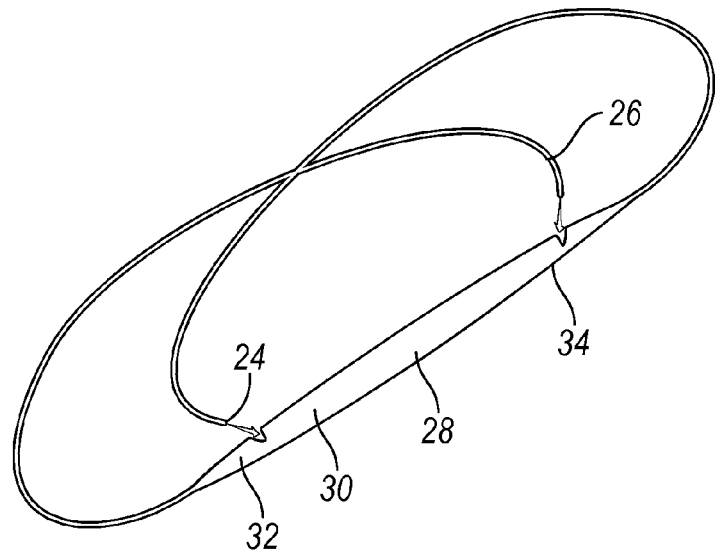
FIG. 3 represents the formation of the suture configuration shown in FIG. 4A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two structures or loops 46 and 46'. Structures defined herein can be loops, knots or tangles, each having unique properties. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 7:
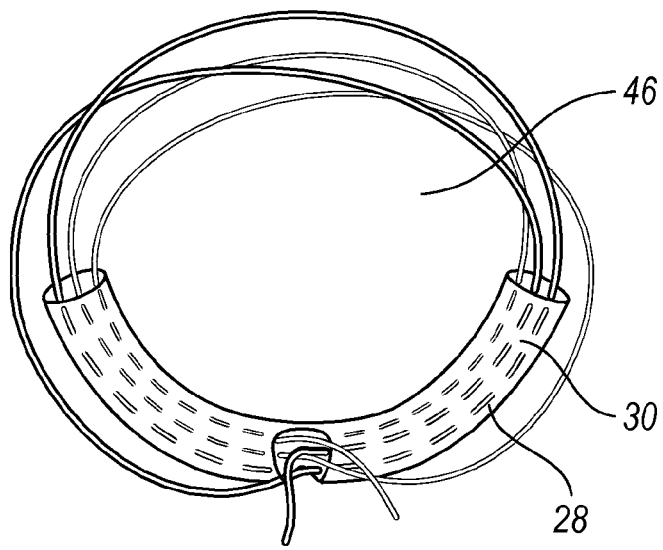
Figure 8:
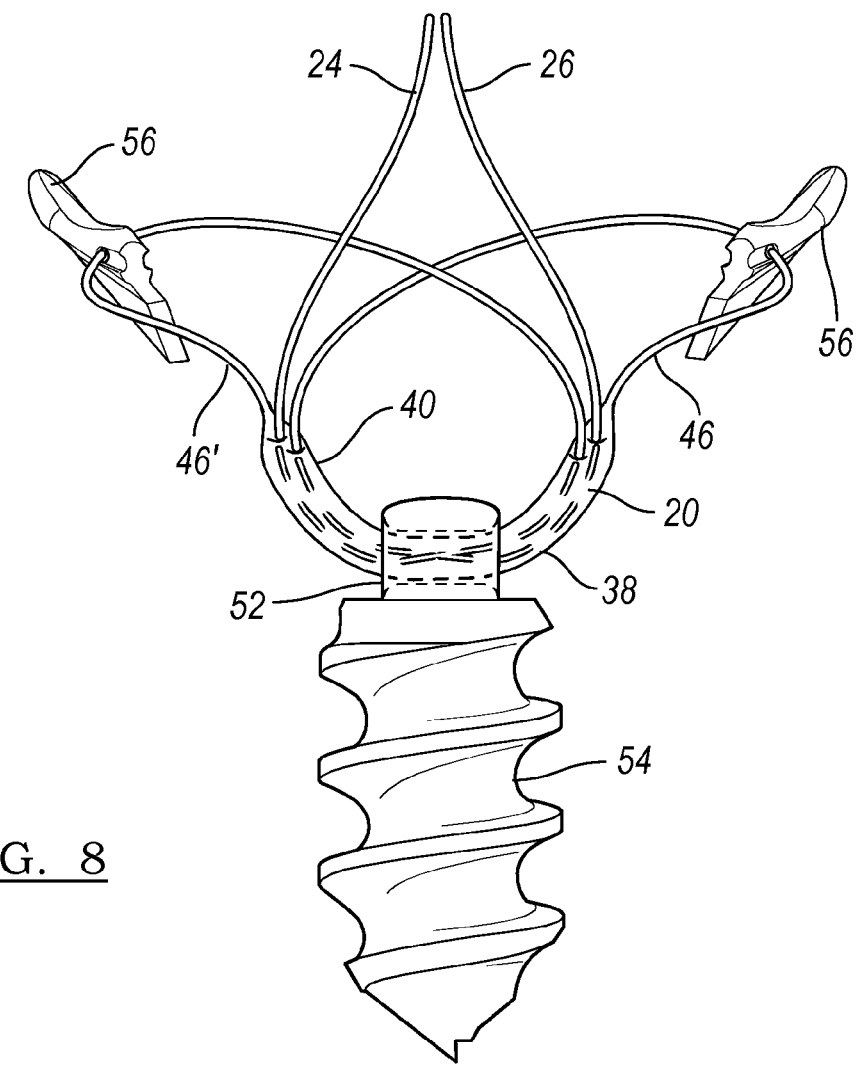
FIG. 8 represents the suture construction according to FIG. 5 coupled to a bone engaging fastener.
Figure 9:
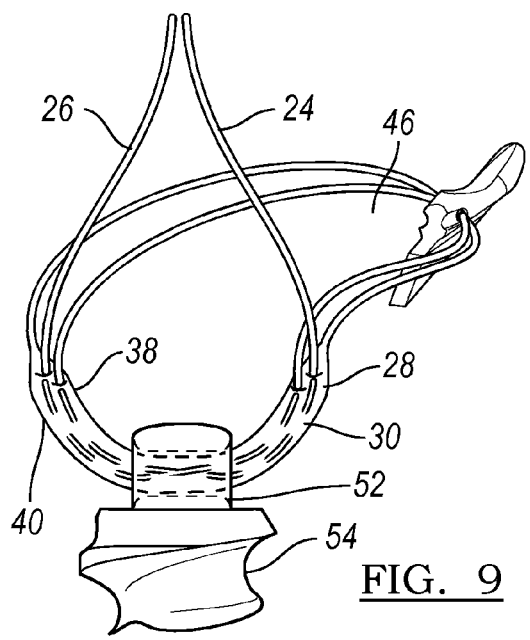
FIGS. 9-11B represent the coupling of the suture construction according to FIG. 5 to a bone screw.
Figure 10:
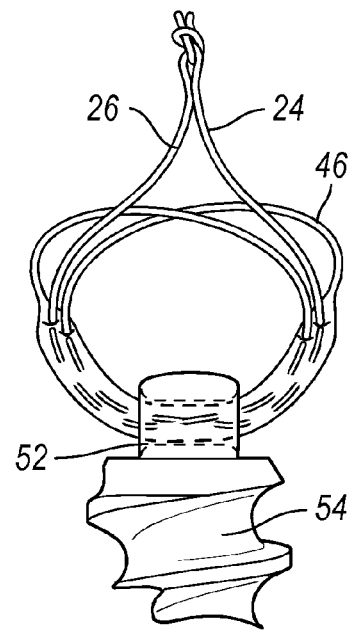

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load. At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11B, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
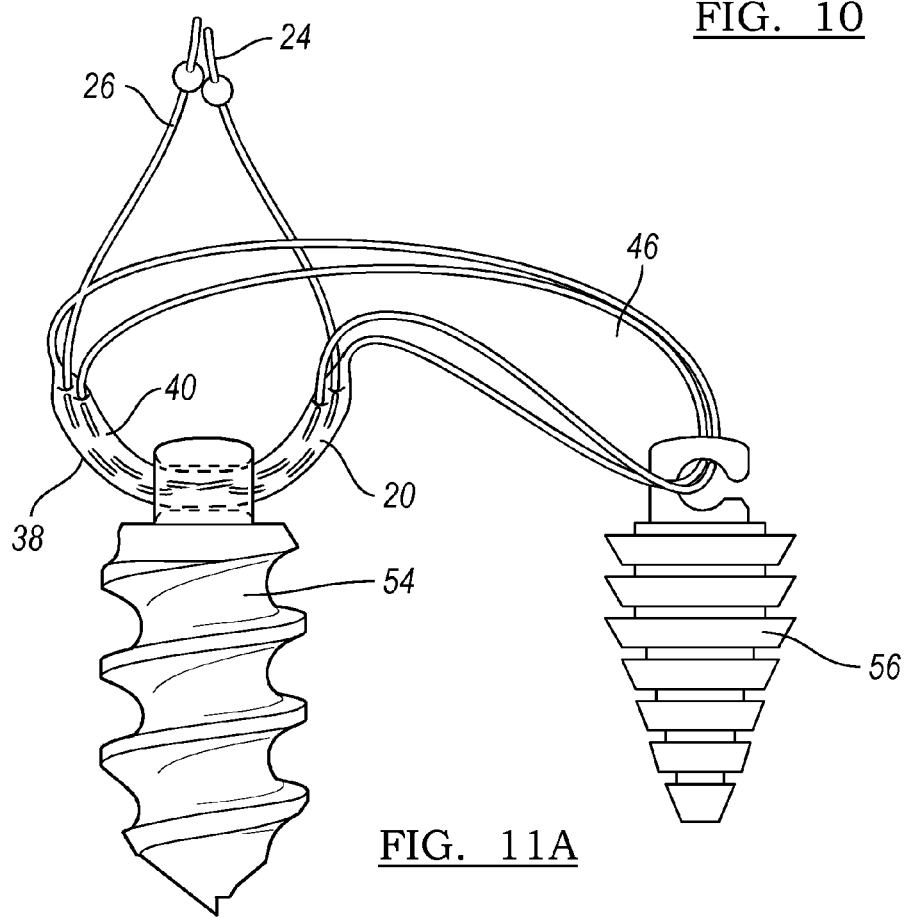
Figure 11B:
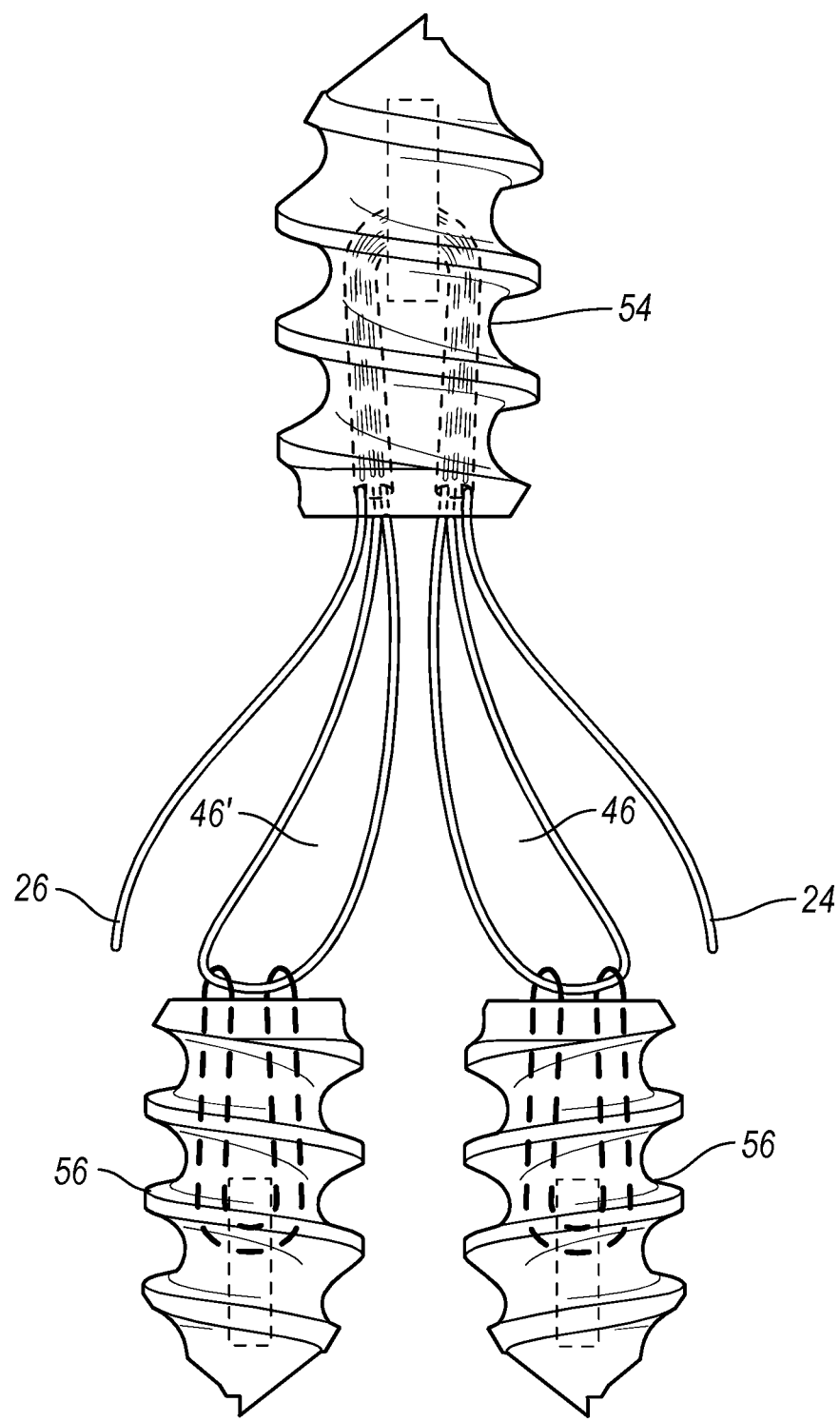

FIG. 11B represents the coupling of the suture construction according to FIG. 2B with a bone fastening member. Coupled to a pair of loops 46 and 46' are tissue fastening members 56. The application of tension to either the first or second end 24 or 26 will tighten the loops 46 or 46' separately.

Figure 12A:
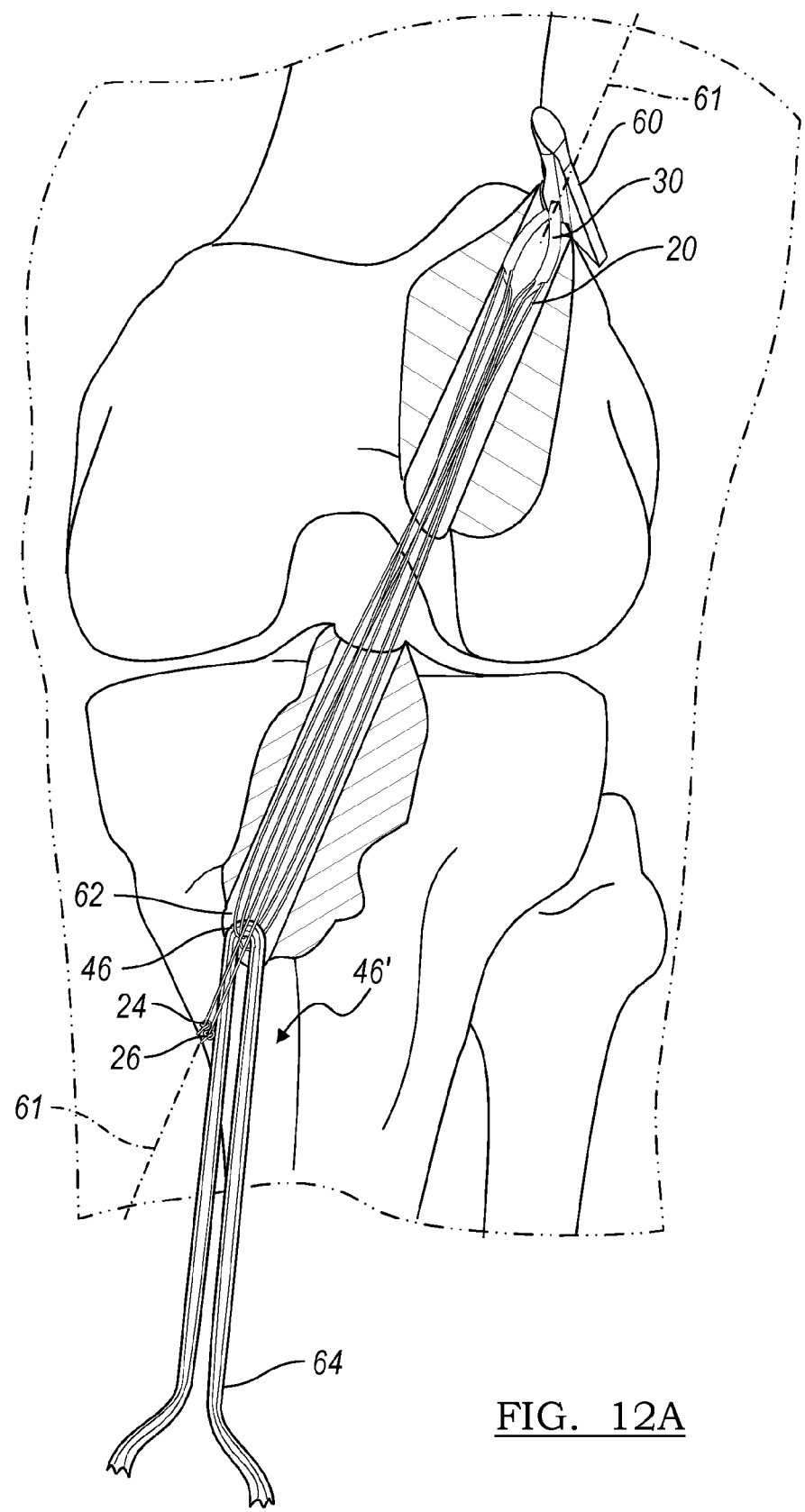
FIGS. 12A-12E represent the coupling of a soft tissue to an ACL replacement in a femoral/tibial reconstruction.
Figure 12B:
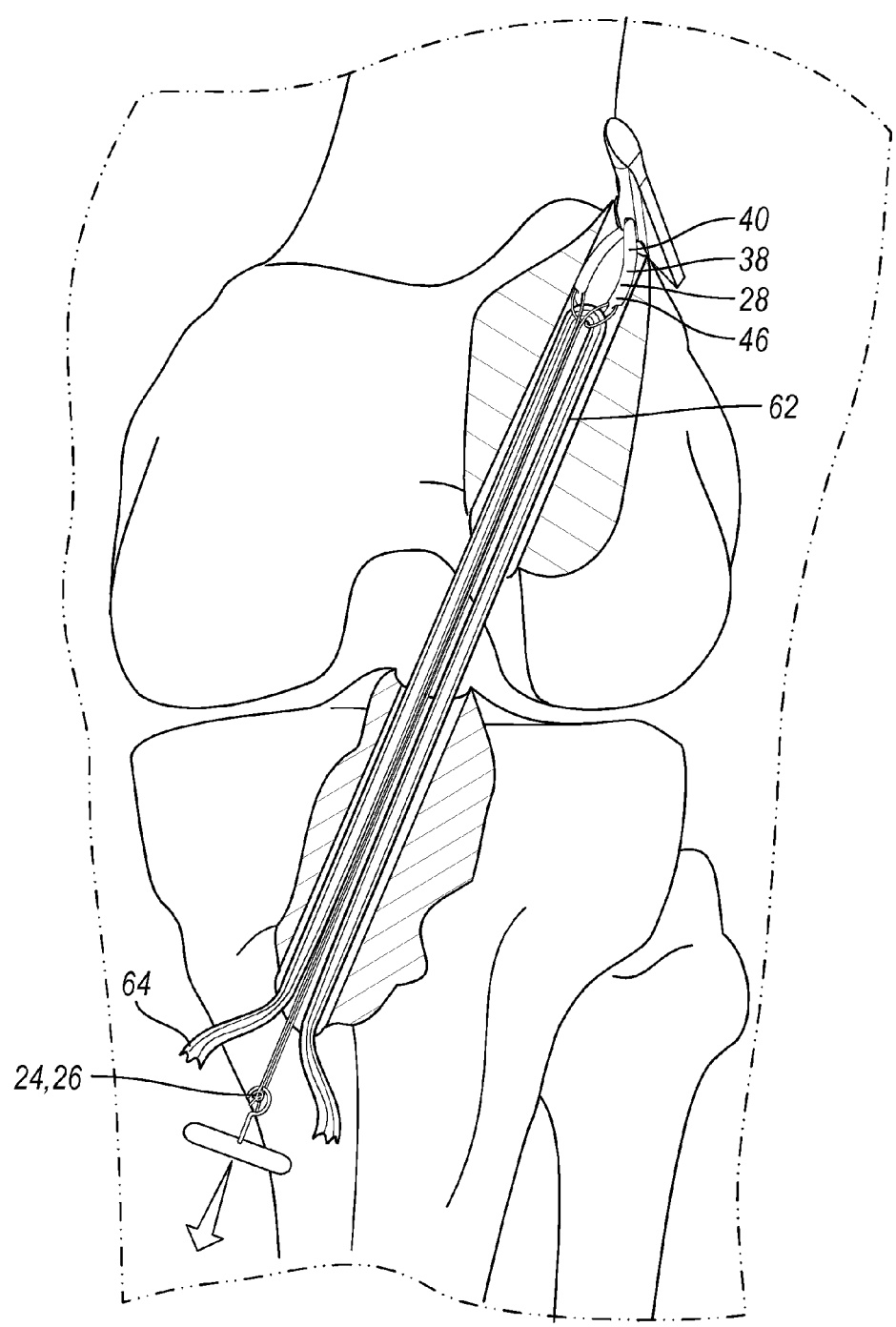

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member 60. The member 60 can have a first profile which allows insertion of the member 60 through the tunnel and a second profile which allows engagement with a positive locking surface upon rotation. The longitudinal passage portion 30 of the suture construction 20, member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the member 60, application of forces to the ends 24, 26 may reduce the seating force applied by the member 60 onto the bone.

Figure 12C:
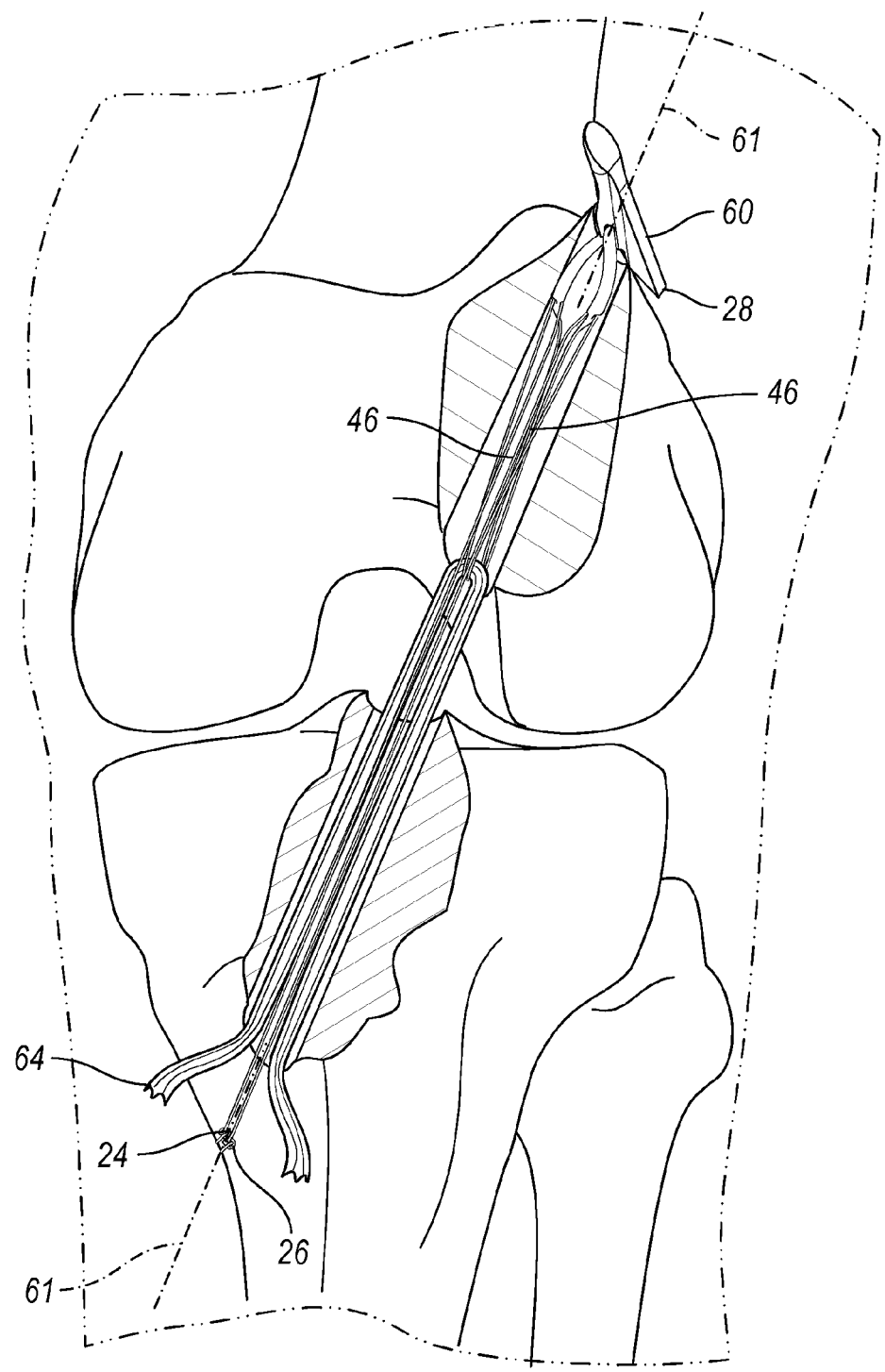
Figure 12D:
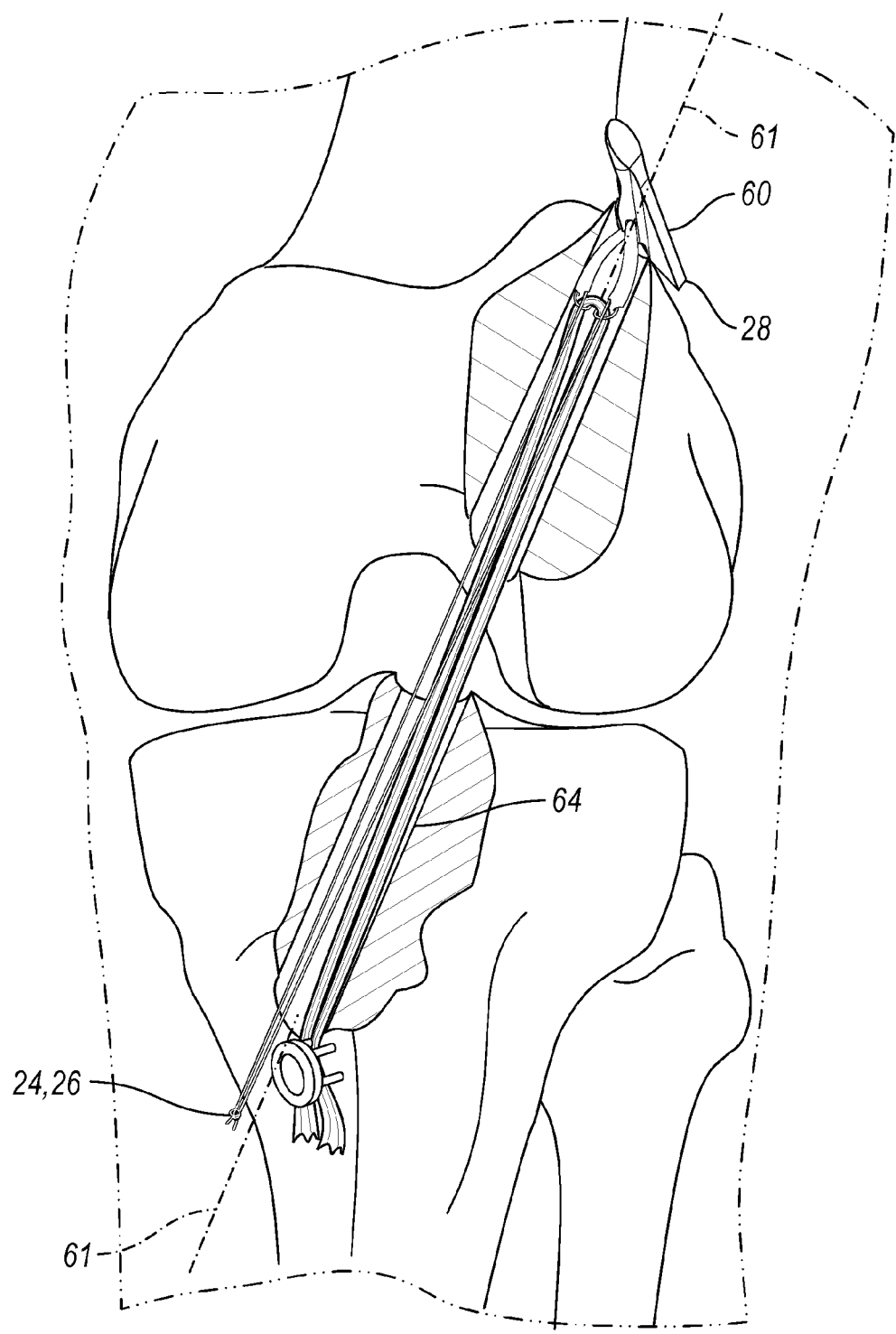

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
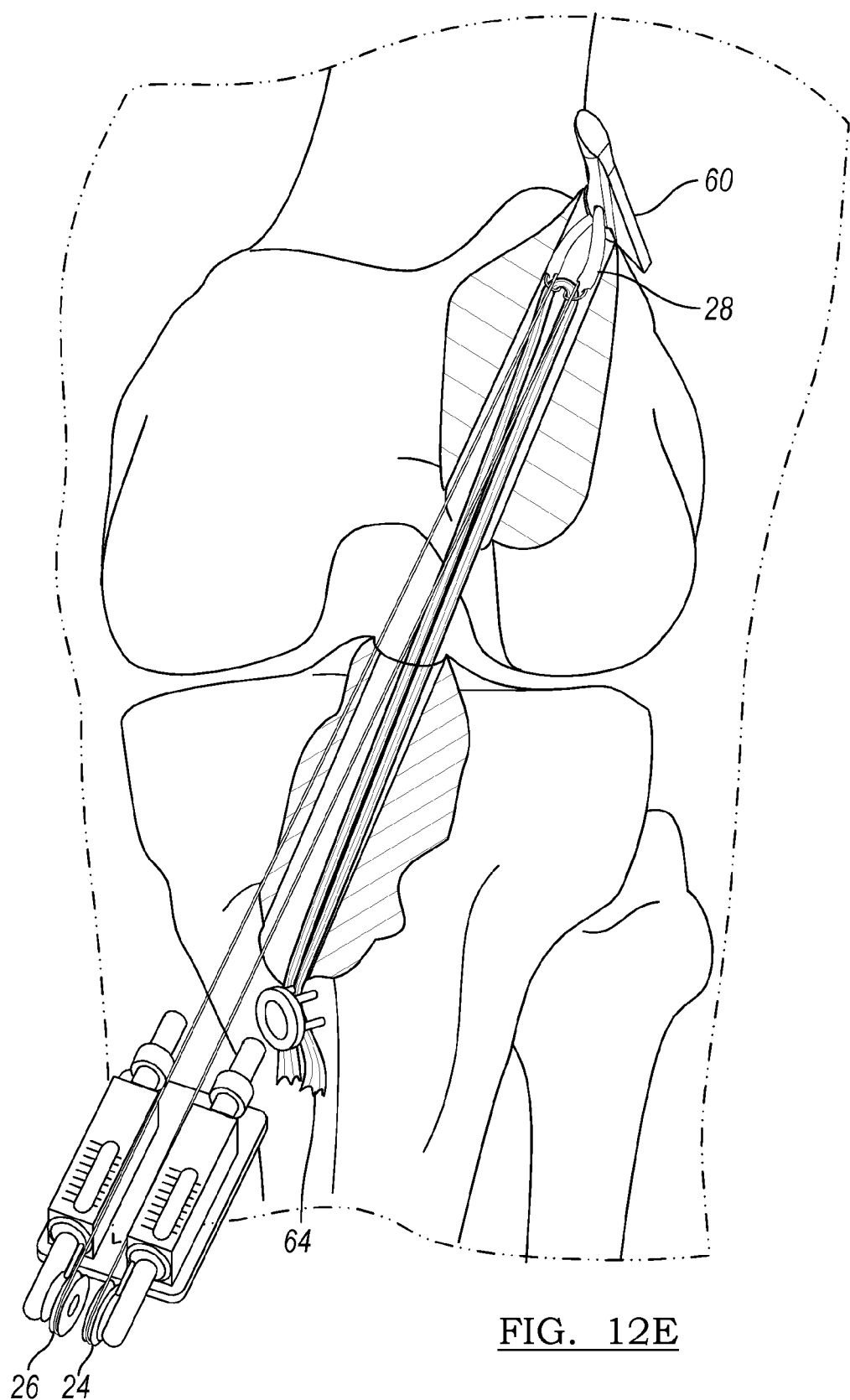
Figure 13A:
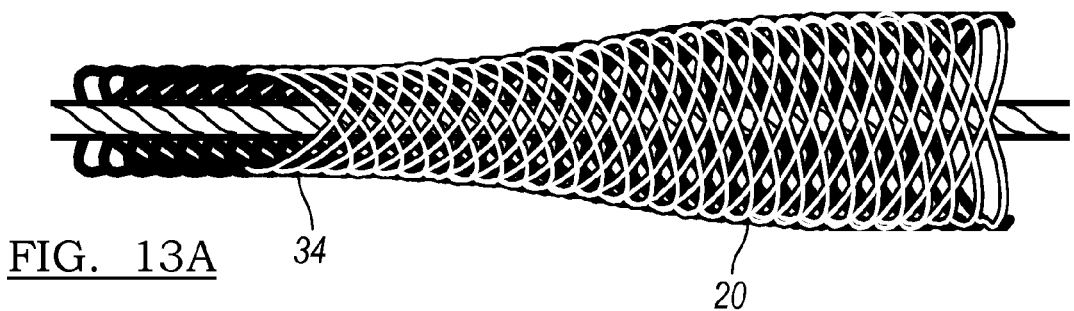
FIGS. 13A-13D represent a close-up view of the suture shown in FIGS. 1-11C.
Figure 13B:
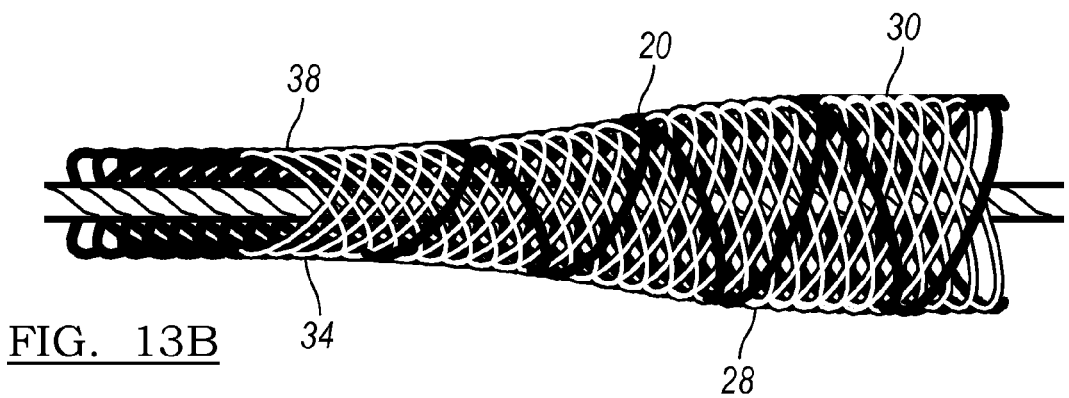
Figure 13C:
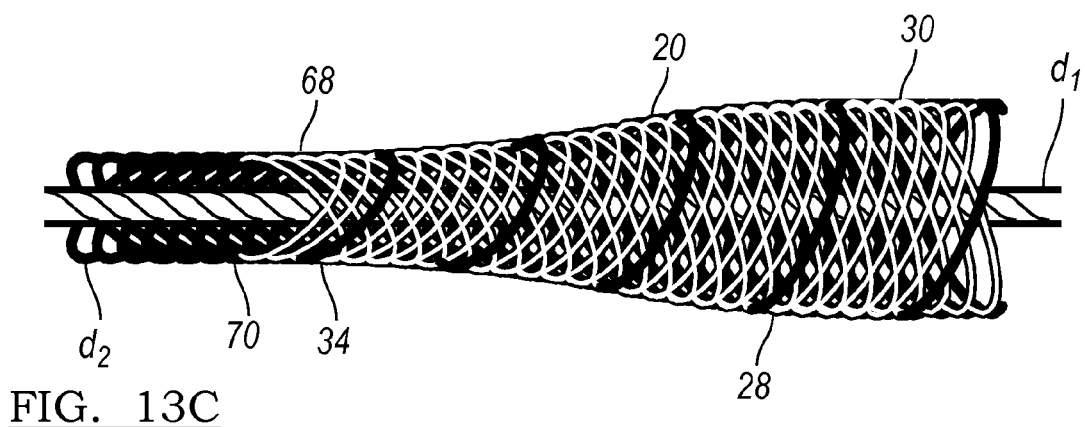
Figure 13D:
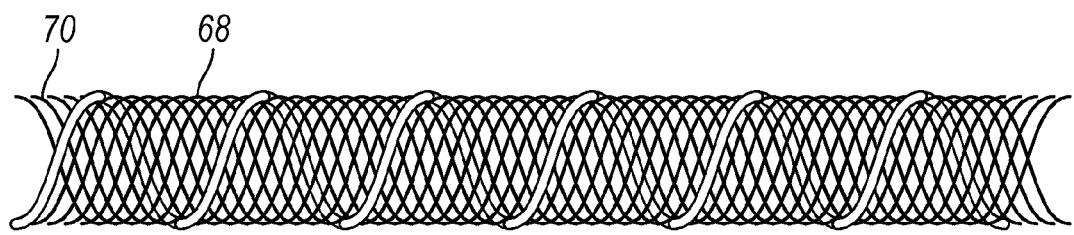

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL. This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14A:
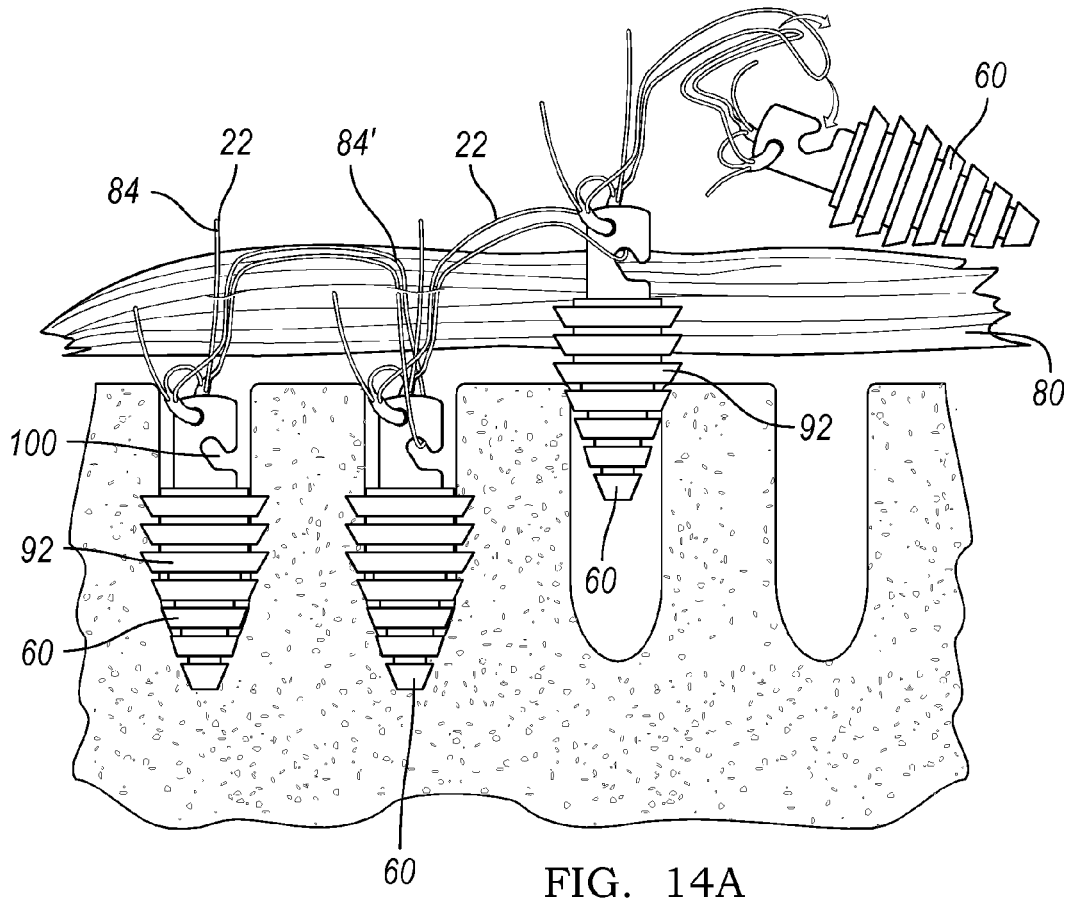
FIGS. 14A and 14B represent side and top views of a suture construction used to couple soft tissue to bone.
Figure 14B:
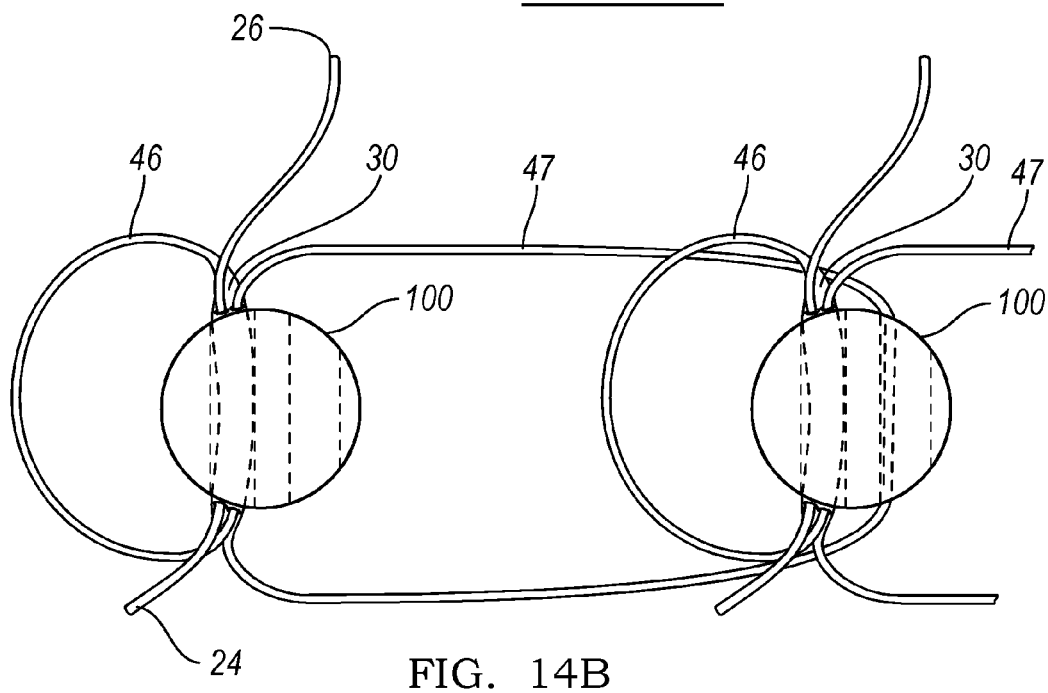

FIGS. 14A and 14B represent the coupling of soft tissue to a bone. Shown is a plurality of bone engaging fasteners 60 coupled to suture constructions 22 shown in FIG. 2A or FIG. 4. Each fastener 60 is coupled to a bone by being pressed into or threaded into an aperture formed within the bone. Adjoining fasteners are coupled together using loops 46 from an adjacent suture construction 22.

The fasteners 60 define a locking feature 92 which is used to couple the fastener 60 to the bone. Disposed on a first end of the fastener 60 is an aperture 94 configured to hold the suture construction 22. Additionally, in the fastener 60 is a locking feature 100 configured to engage with one of the first or second loops 46 or 47 of an adjacent suture construction 22. Returning briefly to FIG. 14A, a suture end 26 and first loop 46 can be passed around or through an aperture 84 in soft tissue.

The first loop 46 is then fed around or through a second aperture 84' formed in the soft tissue 80. After passing through the aperture 84', the first loop 46 is coupled to the coupling feature 100 in an adjacent bone coupling fastener 60. At this point, the first and second ends 24, 26 of the suture 22 are pulled tight, tightening the suture loop 46 about the soft tissue 80. This pulls the soft tissue 80 against a surface of the bone. This can be used to couple soft tissue in an anatomy such in the repair of a rotator cuff.

It is envisioned that a plurality of fasteners 60 can have associated suture constructions 22 which can similarly be coupled to adjacent fasteners 60. Alternatively, the loops 46, 47 can looped around or passed through the soft tissue 80 and then can be coupled to the coupling feature 100 of its fastener 60.

Figure 15A:
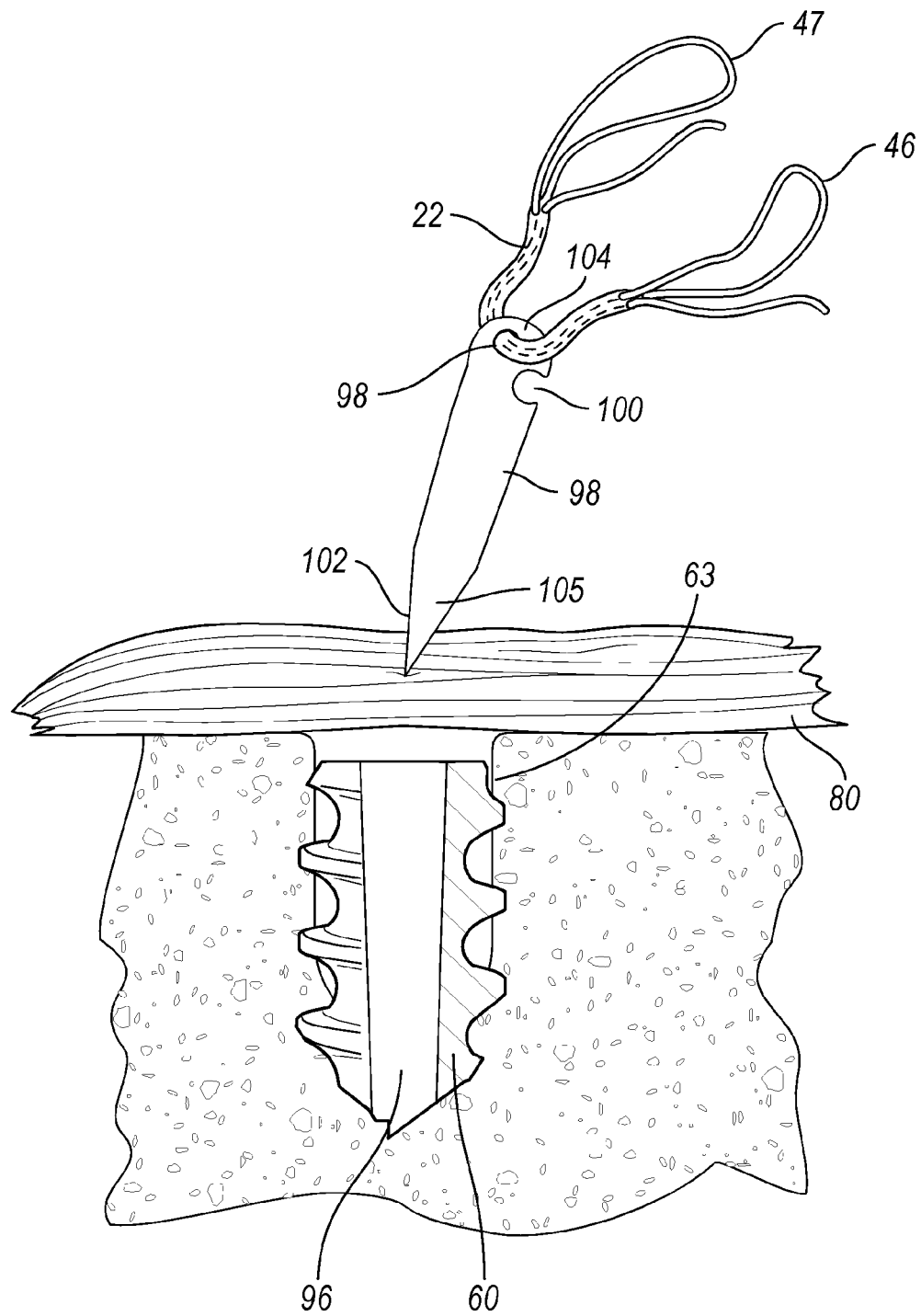
FIGS. 15A-15D represent an alternate method of coupling soft tissue to bone.

FIGS. 15A-15D represent an alternate method of coupling soft tissue 80 to a bone. As shown in FIG. 15A, a first bone coupling fastener 60 is coupled to an aperture 63 formed in the bone. The bone coupling fastener 60 defines a fastener accepting bore 96. The bore 96 may be a through bore or may terminate within the fastener 96. The fastener accepting bore 96 is configured to accept a suture bearing fastener 98. The first loop 46 can be coupled to the second loop 47 to fix the soft tissue 80.

The suture bearing fastener 98 defines an aperture 104 configured to accept the suture construction 22 according to any of the present teachings. As described below, the fastener 98 can also have a concave suture locking feature 100. Disposed at a proximal end 102 of the fastener 96 can be soft tissue piercing feature 105 which can be an acute angle. Additionally, the suture bearing fastener 98 can have locking features to facilitate the coupling to the bore 96 of the bone coupling fastener 60.

Figure 15B:
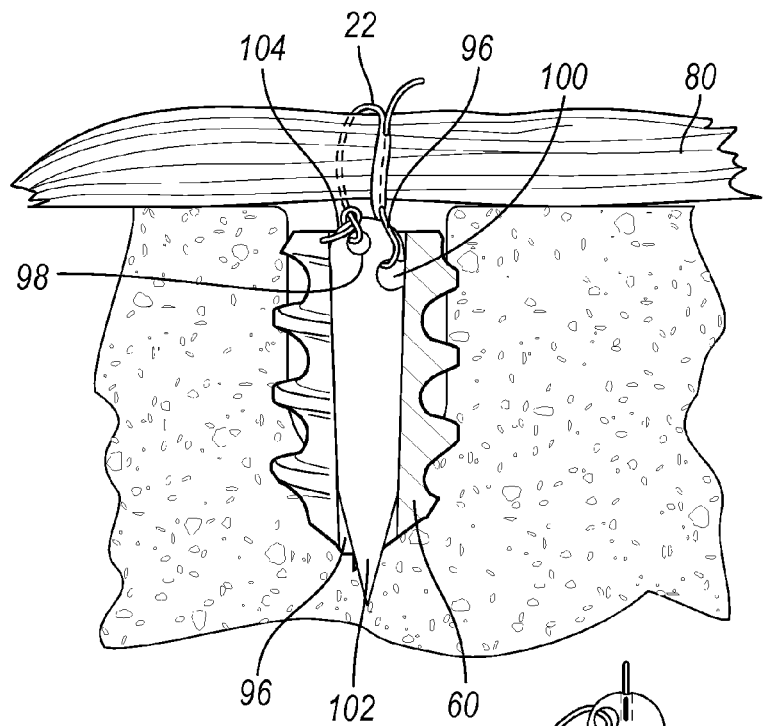

As seen in FIG. 15B, the suture construction of FIGS. 1-7 can be coupled to the suture bearing fastener 98 through the suture bearing aperture 104 using a knot. After the suture bearing fastener 98 is pressed through or adjacent to the soft tissue 80, the suture construction 22 can be looped over the soft tissue 80 and engaged with the concave locking feature 100. The suture bearing fastener 98 can be pressed into the fastener 60 to lock the suture 22 into place. Tension can then be applied to the suture 22 construction to constrict the loop 46 or loops 46 and 47 about the soft tissue 80.

Figure 15D:
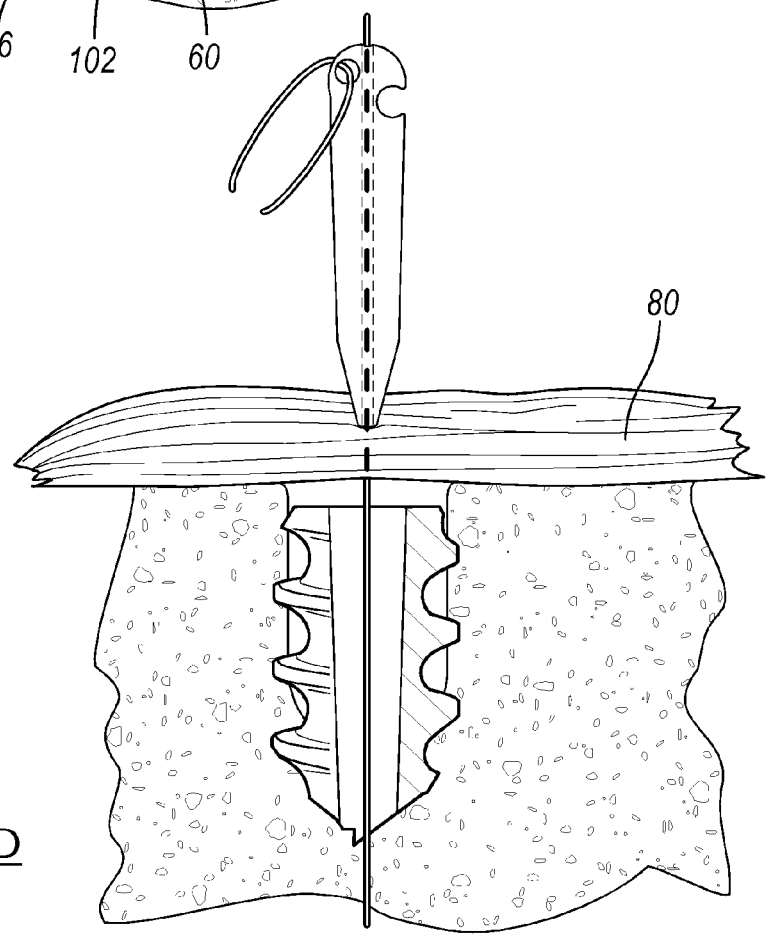
Figure 15C:
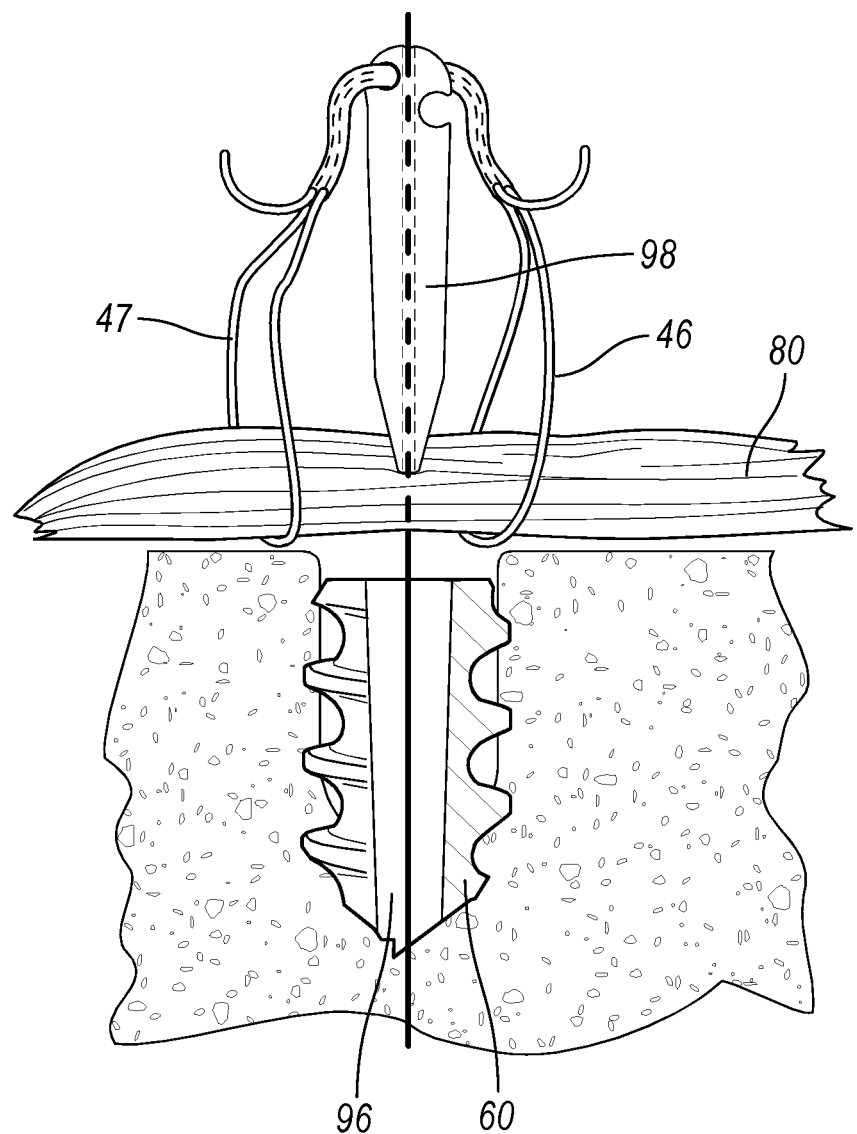

As seen in FIGS. 15C and 15D, the soft tissue 80 can be threaded through the loops 46 and 47 prior to or after the coupling of the suture bearing fastener 98 to the bone engaging fastener 60. A guide wire 99 can be coupled to the bone through the fastener bore 96. The guide wire 99 is then used to align the suture bearing fastener 98 through the soft tissue 80 and into the bore 96 of fastener 60.

As shown in FIG. 16A-16C, one loop 46 of the suture construction 22 can have a fastening element 112 coupled thereto. This fastener element 112 can take the form of a hook having an aperture which accepts the suture from a loop 47. The loop 46 of the suture construction can be passed through the aperture 84 formed in the soft tissue 80.

Figure 16D:
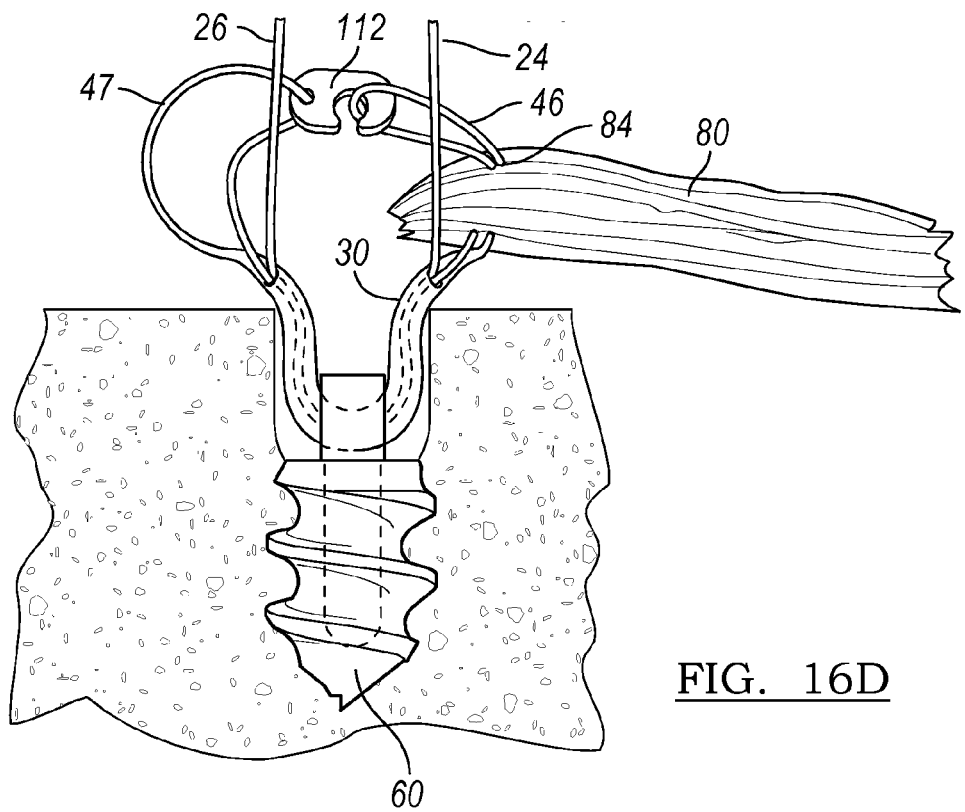

FIG. 16D shows the fastener element 112 can be coupled to the first loop 46. After the first and second loops 46 and 47 are coupled together about the soft tissue 80, tension can be applied to the ends of the construction to pull the soft tissue to the bone.

Figure 17:
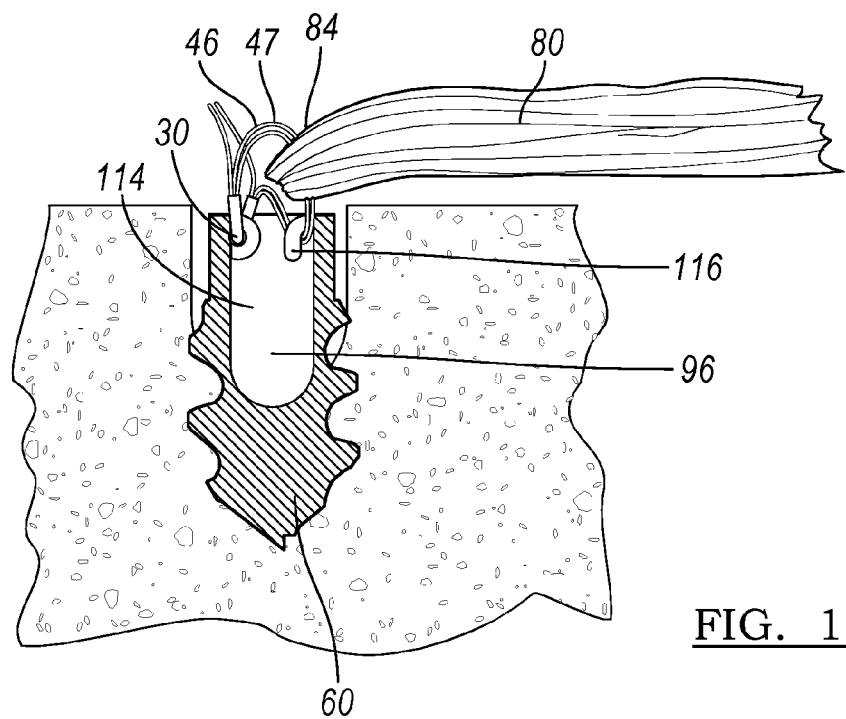
FIG. 17 is an alternate method of coupling soft tissue to bone.

As shown in FIG. 17, bone engaging fastener 60 can have a bore 96 defined therein. The bore 96 can have a defined fastening loop 114 which is used to couple a suture construction 22 to the fastener 60. In this regard, it is envisioned the passage portion 30 of the suture construction can be fixed within the fastening loop. One or both loops 46 and 47 can then be passed though an aperture 84 defined in the soft tissue 80. These loops of material can be hooked to a hook 116 defined within the bore 96. The application of tension to the ends pulls the soft tissue to the bone without the use of knots or additional fasteners.

Figure 18A:
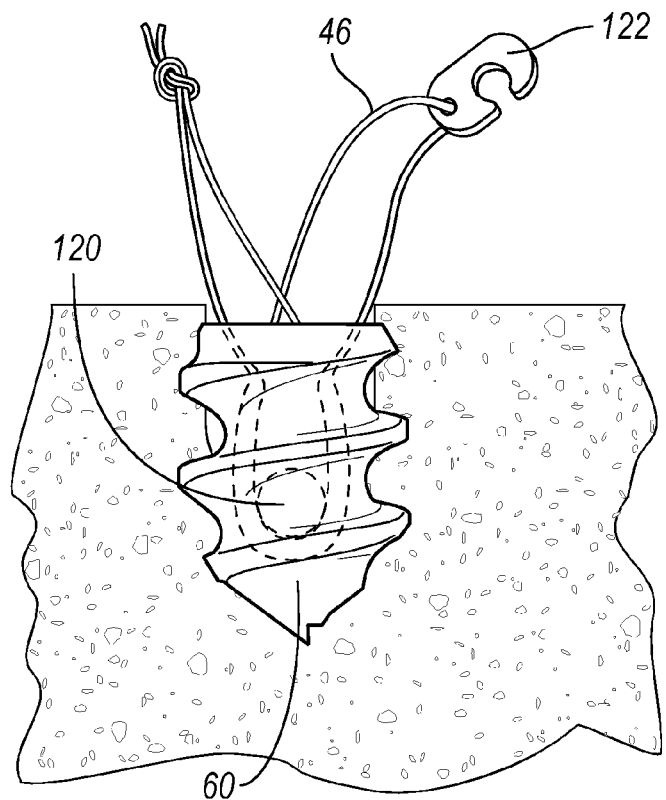
FIGS. 18A-18B represent an alternate mechanism for coupling soft tissue to bone.
Figure 18B:
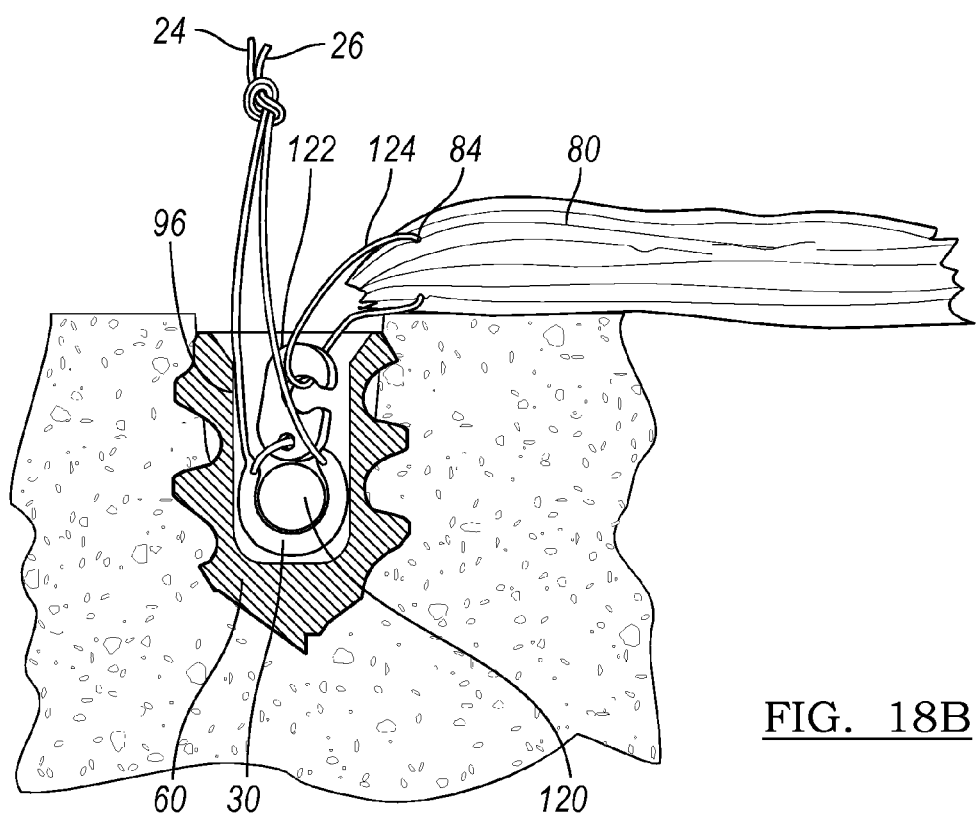

FIGS. 18A and 18B represent an alternate method of coupling soft tissue 80 to bone. Shown is a bone engaging fastener 60 defining an internal bore 96. The internal bore 96 defines a locking mechanism such a through pin 120. Disposed about the locking mechanism is a suture construction 22 having a single loop 46. Disposed on the loop 46 is a locking hook 122.

As shown in FIG. 18B, the locking hook 122 can be used to couple the fastener 60 to a suture loop 124 passed through an aperture 84 formed in soft tissue 80. The application of tension to the ends 22 and 26 of the suture construction 22 pulls the locking hook 122 and suture 124 into the bore 96, thus locking the soft tissue 80 to the bone.

Figure 19A:
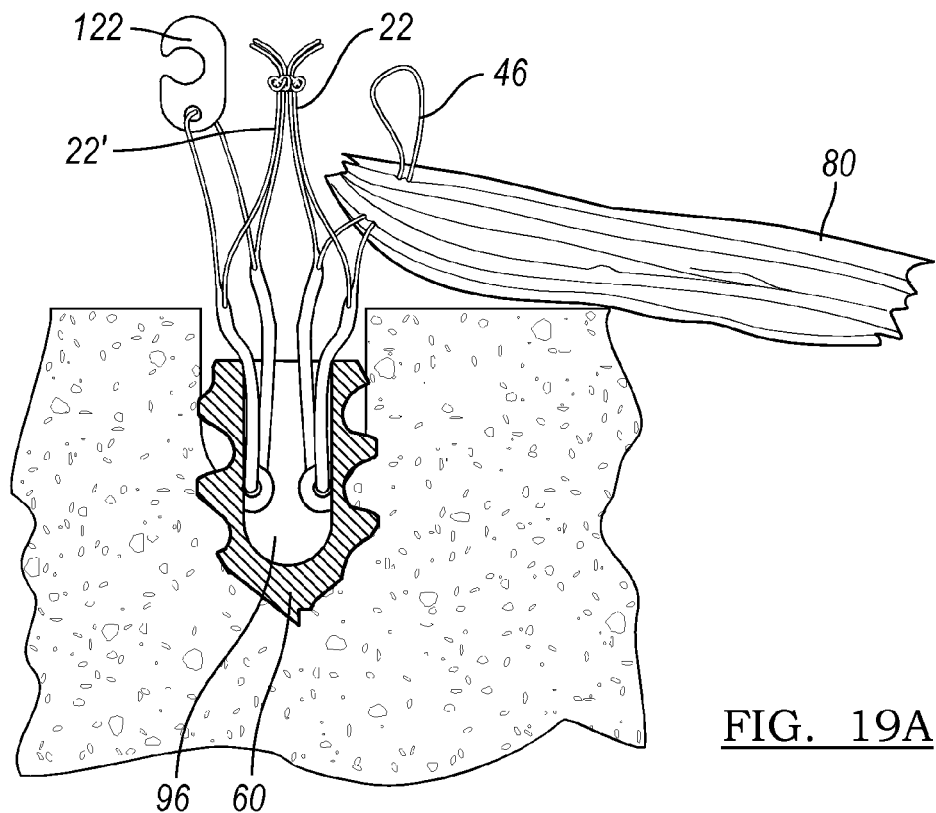
FIGS. 19A-19C represent another method of coupling soft tissue to bone.
Figure 19B:
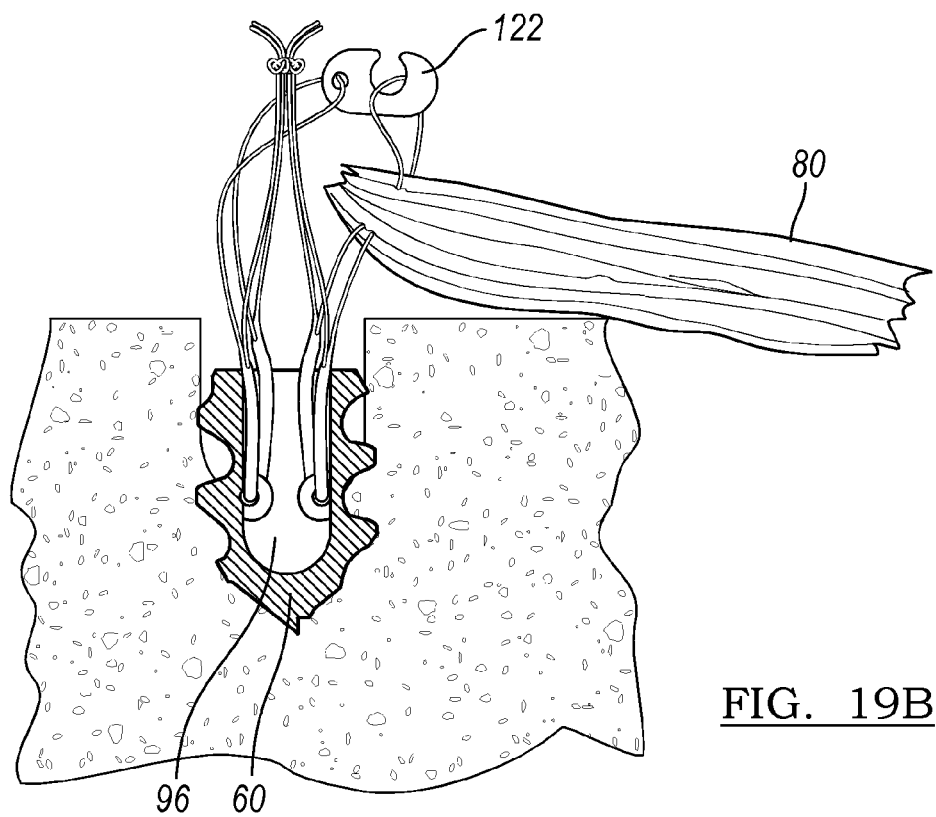
Figure 19C:
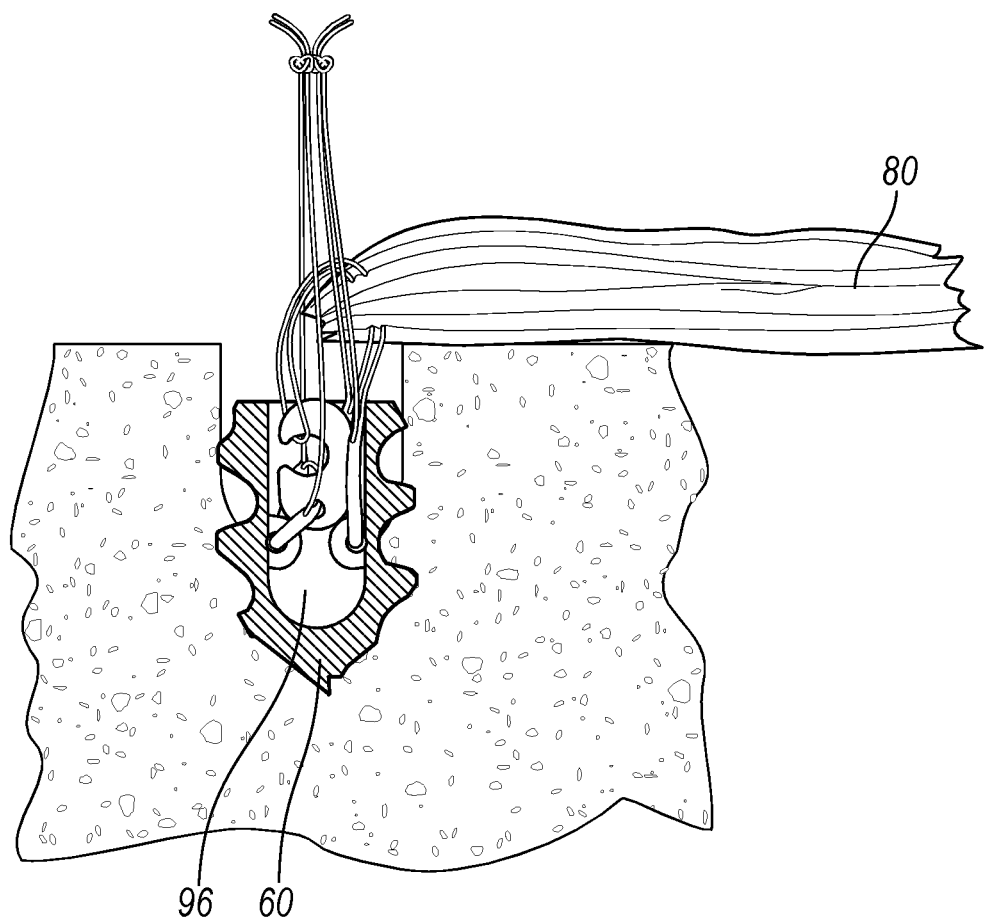

As seen in FIGS. 19A-19C, the fastener 60 can have a pair of suture constructions 22 and 22'. The first suture 22 can have a coupling member 122, while the second suture 22' can have a loop 46 threaded through the soft tissue 80. After the loop 46 is threaded through or around the soft tissue, the locking member 122 is coupled to the loop 46. The application of tension to the ends 26 of the suture constructions 22 and 22' pull the locking member 122 into a bore 96 formed by the fastener 60. This locks the loop 46 into position. Tension on the end 26 of suture 22 then pulls the soft tissue to the bone.

It should be noted that while the interior bore of the fasteners 60 is shown as being smooth, it is envisioned that the interior surface can have features such as barbs or locking tabs to facilitate the coupling of the suture engaging fastener 98 with the bone engaging fastener 60. Additionally, the interior bores can define driving surfaces or features such as a hex head.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices, e.g. humeral, femoral or tibial stems. Such variations are not to be regarded as a departure from the spirit and scope of the invention.

What is claimed is:

1. A method of coupling a soft tissue to a bone, comprising:
   determining an area of the bone to couple a first anchor and a second anchor, wherein: (i) the first anchor includes a first bone engaging feature, a first aperture, and a first suture member, the first suture member including a braided body disposed in the first aperture and defining a longitudinally extending passage having a plurality of passage apertures, and a first end extending from the braided body and passing through a passage aperture, through the passage and out another passage aperture, so as to place the first end outside of the passage, and define an adjustable first loop, and a second end extending from the braided body and passing through a passage aperture, through the passage and out another passage aperture, so as to place the second end outside of the passage, and define an adjustable second loop, and (ii) the second anchor includes a second bone engaging feature and a first coupling feature;
   forming a first hole in the area;
   forming a second hole in the area adjacent to the first hole;
   positioning the first anchor in the first hole;
   positioning the second anchor in the second hole;
   coupling the first loop to the soft tissue;
   coupling the first loop to the first coupling feature; and
   adjusting a size and tensioning the first loop to compress the soft tissue against the bone by pulling on the first end of the first suture member, after the first anchor is positioned in the first hole and after the second anchor is positioned in the second hole.

2. The method according to claim 1, further comprising passing the first loop through the soft tissue.

3. The method according to claim 2, further comprising passing the first loop through the soft tissue prior to coupling the first loop to the first coupling feature.

4. The method according to claim 3, further comprising:
   passing the first end through the first loop; and
   passing the first end through the soft tissue.

5. The method according to claim 1, further comprising looping the first loop around the soft tissue.

6. The method according to claim 5, further comprising looping the first loop around the soft tissue prior to coupling the first loop to the first coupling feature.

7. The method according to claim 1, wherein the first coupling feature includes a hook configured to receive the first loop, and wherein coupling the first loop to the first coupling feature includes coupling the first loop to the hook after the second anchor is positioned in the second hole.

8. The method according to claim 1, the method further comprising:
   passing the soft tissue through the second loop; and
   adjusting a size of the second loop to compress the soft tissue against the bone by pulling on the second end after the first anchor is positioned in the first hole and after the second anchor is positioned in the second hole.

9. The method according to claim 1, the method further comprising:
   coupling the second loop to the soft tissue; and
   coupling the second loop to one of the first coupling feature or the second coupling feature.

10. The method according to claim 1, the method further comprising:
    coupling the second loop to a third anchor in the bone adjacent to the first anchor.

11. A method of coupling a soft tissue to a bone, comprising:
    determining an area of the bone to couple a first anchor, a second anchor, and a third anchor, wherein: (i) the first anchor includes a first bone engaging feature and a first suture member coupled to the first anchor and forming an adjustable first loop, where the first suture member includes: (a) a first braided body defining a longitudinally extending first passage, and a first end extending from the first braided body and passing through a first aperture in the braided body and along the first passage and out a second aperture in the braided body so as to place the first end outside of the first passage, and define the first loop; and (b) a second end extending from the braided body and passing through the second aperture in the braided body and along the first passage and out the first aperture in the braided body so as to place the second end outside of the first passage, and define a second loop, (ii) the second anchor includes a second bone engaging feature, a first coupling feature, and a second suture member coupled to the second anchor and forming an adjustable third loop; and (iii) the third anchor includes a third bone engaging feature and a second coupling feature;
    positioning the first anchor, the second anchor, and the third anchor in the bone adjacent to each other in the area;
    coupling the first loop to the soft tissue and to the first coupling feature of the second anchor, wherein the first loop is coupled to the second anchor after the first anchor and the second anchor have been positioned in the bone; and
    coupling the third loop to the soft tissue and to the second coupling feature of the third anchor, wherein the third loop is coupled to the third anchor after the second anchor and third anchor have been positioned in the bone.

12. The method according to claim 11, further comprising passing the third loop through the first loop.

13. The method according to claim 11, further comprising passing at least one of the first loop or the third loop through the soft tissue.

14. The method according to claim 13, further comprising looping at least one of the first loop or the third loop around the soft tissue.

15. The method according to claim 11, further comprising:
adjusting a first size of the first loop to compress the soft tissue against the bone by pulling on a first end of the first suture member after the first anchor and the second anchor are positioned in the bone; and
adjusting a second size of the third loop to compress the soft tissue against the bone by pulling on a third end of the second suture member after the second anchor and the third anchor are positioned in the bone.

16. The method according to claim 11, further comprising passing the soft tissue through the first loop and the third loop.

17. The method according to claim 11, wherein:
the second suture member includes: a second braided body coupled to the second anchor defining a longitudinally extending second passage, and a third end extending from the second braided body and passing through a first aperture in the second braided body and along the second passage and out a second aperture in the second braided body so as to place the third end outside of the second passage, and define the third loop.

18. The method of claim 11, further comprising:
passing the soft tissue through the third loop; and
adjusting a size of the third loop to compress the soft tissue against the bone by pulling on a third end.

19. The method of claim 11, wherein the first anchor further includes a third coupling feature, the method further comprising:
coupling the second loop to the soft tissue; and
coupling the second loop to the third coupling feature.

20. A method of coupling a soft tissue to a bone, comprising:
determining an area of the bone to couple a first anchor, a second anchor, and a third anchor wherein: (i) the first anchor includes a first bone engaging feature, a first aperture, and a first suture member, the first suture member including a first braided body disposed in the first aperture and defining a longitudinally extending first passage, and a first end extending from the first braided body and passing into the first passage and and out the first passage so as to place the first end outside of the first passage, and define a self-locking, adjustable first loop, and a second end extending from the first braided body and passing into the first passage and out the first passage so as to place the second end outside of the first passage, and define a self-locking, adjustable second loop, (ii) the second anchor includes a second bone engaging feature, a second aperture, a first hook feature, and a second suture member, the second suture member including a second braided body disposed in the second aperture and defining a longitudinally extending second passage, and a third end extending from the second braided body and passing into the second passage and out the second passage so as to place the third end outside of the second passage, and define a self-locking, adjustable third loop, and a fourth end extending from the second braided body and passing into the second passage and out the second passage so as to place the fourth end outside of the second passage, and define a self-locking, adjustable fourth loop, and (iii) the third anchor includes a third bone engaging feature and a second hook feature;
forming a first hole, a second hole, and a third hole adjacent to each other in the area;
positioning the first anchor, the second anchor, and the third anchor in the first hole, the second hole, and the third hole, respectively;
coupling the first loop and the third loop to the soft tissue;
coupling the first loop to the first hook feature;
passing the third loop through the first loop;
coupling the third loop to the second hook feature; and
tensioning the first loop and the third loop to compress the soft tissue against the bone by pulling on the first end of the first suture member and the third end of the second suture member after the first anchor is positioned in the first hole, after the second anchor is positioned in the second hole, and after the third anchor is positioned in the third hole.

21. The method of claim 20, wherein the bone is a shoulder bone and the soft tissue is a rotator cuff, and wherein coupling the first loop and the third loop to the soft tissue includes coupling the first loop and the third loop to the rotator cuff.

* * * * *

UNITED STATES PATENT AND TRADEMARK OFFICE
CERTIFICATE OF CORRECTION

PATENT NO.       : 8,551,140 B2
APPLICATION NO.  : 13/181729
DATED            : October 8, 2013
INVENTOR(S)      : Gregory J. Denham It is certified that error appears in the above-identified patent and that said Letters Patent is hereby corrected as shown below:

On the Title Page

Item (56), References Cited, Other Publications, Column 1, line 30, (Information Disclosure Statement dated January 10, 2012, Form 1449, page 32, Non Patent Literature Documents, Reference No. CB); Delete "lntrafix" and insert --Intrafix--.

Item (56), References Cited, Other Publications, Column 1, line 30, (Information Disclosure Statement dated January 10, 2012, Form 1449, page 32, Non Patent Literature Documents, Reference No. CB); Delete "Fasteners," and insert --Fasteners),--.

Item (56), References Cited, Other Publications, Column 1, line 33, (Information Disclosure Statement dated January 10, 2012, Form 1449, page 32, Non Patent Literature Documents, Reference No. CC); Delete "Mitek,(Feb." and insert --Mitek (Feb.--.

Item (56), References Cited, Other Publications, Column 2, line 6, (Information Disclosure Statement dated January 10, 2012, Form 1449, page 32, Non Patent Literature Documents, Reference No. CN); Delete "et al;" and insert --et al.,--.

Item (56), References Cited, Other Publications, Column 2, line 16, (Information Disclosure Statement dated January 10, 2012, Form 1449, page 32, Non Patent Literature Documents, Reference No. CS); Delete "al." and insert --al.,--.

Item (56), References Cited, Other Publications, Column 2, line 19, (Information Disclosure Statement dated January 10, 2012, Form 1449, page 32, Non Patent Literature Documents, Reference No. CT); Delete "AT," and insert --A. T.,--.

Item (56), References Cited, Other Publications, Column 2, line 70, (Information Disclosure Statement dated December 14, 2012, Form 1449, page 32, Non Patent Literature Documents, Reference No. CE); Delete "mailedOct." and insert --mailed Oct.--.

In the Drawings

Sheet 19, Reference No. 22, FIG. 19A, (Drawings - only, page 19, black and white, dated July 13, 2011); Delete "22" and insert --22'--.

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,551,140 B2

Sheet 19, Reference No. 22', FIG. 19A, (Drawings - only, page 19, black and white, dated July 13, 2011); Delete "22'" and insert --22--.

In the Specifications

Column 5, Line 46 (Specification, Page 12, Line 3); Delete "94" and insert --84--.

Column 5, Line 61 (Specification, Page 12, Line 7); After "such", insert --as--.

Column 6, Line 6 (Specification, Page 13, Line 5); Delete "96" and insert --60--.

Column 6, Line 36 (Specification, Page 14, Line 1); Delete "FIG." and insert --FIGS.--.

Column 7, Line 1 (Specification, Page 15, Line 3); Delete "22" and insert --24--.

Column 7, Line 2 (Specification, Page 15, Line 4); After "suture", insert --loop--.

In the Claims

Column 9, Line 9, Claim 14 (Response After Final Action, Page 6, Line 1, Claim 16, Response dated May 13, 2013); In Claim 14, Delete "13," and insert --11,--.

Column 10, Line 4, Claim 20 (Response After Final Action, Page 7, Line 6, Claim 20, Response dated May 13, 2013); In Claim 20, Before "out", delete "and".